United States Patent
Fukuda et al.

(10) Patent No.: US 10,927,401 B2
(45) Date of Patent: Feb. 23, 2021

(54) METHOD FOR EXTRACTING SUBSTANCE FROM FECES SAMPLE

(71) Applicant: KEIO UNIVERSITY, Tokyo (JP)

(72) Inventors: Shinji Fukuda, Yamagata (JP); Chiharu Ishii, Yamagata (JP); Masaru Tomita, Yamagata (JP)

(73) Assignee: Keio University, Tokyo (JP)

( * ) Notice: Subject to any disclaimer, the term of this patent is extended or adjusted under 35 U.S.C. 154(b) by 446 days.

(21) Appl. No.: 15/758,087

(22) PCT Filed: Sep. 8, 2016

(86) PCT No.: PCT/JP2016/004104
§ 371 (c)(1),
(2) Date: May 24, 2018

(87) PCT Pub. No.: WO2017/043087
PCT Pub. Date: Mar. 16, 2017

(65) Prior Publication Data
US 2018/0305736 A1    Oct. 25, 2018

(30) Foreign Application Priority Data
Sep. 11, 2015    (JP) .............................. JP2015-179076

(51) Int. Cl.
*C12Q 1/6806*    (2018.01)
*G01N 30/06*    (2006.01)
(Continued)

(52) U.S. Cl.
CPC ......... *C12Q 1/6806* (2013.01); *G01N 1/4055* (2013.01); *G01N 30/06* (2013.01);
(Continued)

(58) Field of Classification Search
CPC .. C12Q 1/6806; C12Q 1/6876; G01N 1/4055; G01N 33/6848; G01N 30/06;
(Continued)

(56) References Cited

U.S. PATENT DOCUMENTS

| | | | |
|---|---|---|---|
| 8,697,036 B2* | 4/2014 | Hoke, II | A61K 8/55 424/49 |
| 2011/0081363 A1* | 4/2011 | Whitney | A01N 1/0231 424/184.1 |

(Continued)

FOREIGN PATENT DOCUMENTS

| | | |
|---|---|---|
| JP | 2008-005778 | 1/2008 |
| JP | 2012-080853 | 4/2012 |

(Continued)

OTHER PUBLICATIONS

Marcobal et al., "A metabolomic view of how the human gut microbiota impacts the host metabolome using humanized and gnotobiotic mice," Jun. 6, 2013, 7 ed., 10 issu., p. 1933-1943 (Year: 2013).*

(Continued)

*Primary Examiner* — Jennifer Wecker
*Assistant Examiner* — Michael Paul Shimek
(74) *Attorney, Agent, or Firm* — Occhiuti & Rohlicek LLP

(57) ABSTRACT

A method for extracting substances from a fecal sample using mass spectrometry or nuclear magnetic resonance spectrometry, and metagenomic analysis using a next-generation sequencer. The method includes step A: a step of suspending the fecal sample in any one of the following solvents (a) to (g) to obtain a suspension: (a) a solvent comprising an aqueous solvent and a hydrophilic organic solvent; (b) a solvent comprising an aqueous solvent and a hydrophobic organic solvent; (c) a solvent comprising an (Continued)

aqueous solvent, a hydrophilic organic solvent and a hydrophobic organic solvent; (d) a solvent comprising a hydrophilic organic solvent; (e) a solvent comprising a hydrophobic organic solvent; (f) a solvent comprising a hydrophilic organic solvent and a hydrophobic organic solvent; and (g) a solvent consisting of water; step B: a step of separating a liquid layer comprising the solvent from the suspension; and step C: a step of removing proteins from the liquid layer and then obtaining the one or more substances.

11 Claims, 11 Drawing Sheets

(51) Int. Cl.
| | |
|---|---|
| *C12Q 1/6876* | (2018.01) |
| *G01N 1/40* | (2006.01) |
| *G01N 33/68* | (2006.01) |
| G01N 1/38 | (2006.01) |
| A61B 10/00 | (2006.01) |
| C12N 15/10 | (2006.01) |

(52) U.S. Cl.
CPC ...... *G01N 33/6848* (2013.01); *A61B 10/0038* (2013.01); *C12N 15/1003* (2013.01); *C12Q 1/6876* (2013.01); *G01N 2001/386* (2013.01); *G01N 2001/4061* (2013.01); *G01N 2030/062* (2013.01)

(58) Field of Classification Search
CPC ..... G01N 2001/4061; G01N 2001/386; G01N 2030/062; A61B 10/0038; C12N 15/1003
See application file for complete search history.

(56) References Cited

U.S. PATENT DOCUMENTS

| | | | |
|---|---|---|---|
| 2011/0244461 A1 | 10/2011 | Tanigami et al. | |
| 2011/0281272 A1* | 11/2011 | Klein | C12N 15/1006 435/6.12 |
| 2012/0100542 A1 | 4/2012 | Nagaoka et al. | |

FOREIGN PATENT DOCUMENTS

| | | |
|---|---|---|
| JP | 2014-61459 | 4/2014 |
| WO | WO 2014/045932 | 3/2014 |

OTHER PUBLICATIONS

Arthur et al., "Intestinal Inflammation Targets Cancer-Inducing Activity of the Microbiota." Science, Oct. 5, 2012, vol. 338, pp. 120-123, 5 pages. Downloaded from http://science.sciencemag.org on Apr. 19, 2018.
Dietmair et al., "Towards quantitative metabolomics of mammalian cells: development of a metabolite extraction protocol." Analytical Biochemistry 404, 2010, pp. 155-164.
Furusawa et al., "Commensal microbe-derived butyrate induces the differentiation of colonic regulatory T cells." Nature, Dec. 19, 2013, 504(7480), pp. 446-450, Abstract Only, 1 page.
Garrett et al., "Communicable Ulcerative Colitis Induced by T-bet Deficiency in the Innate Immune System." Cell, 131, Oct. 5, 2007, pp. 33-45.
Human Metabolome Technologies, Metabolomics at HMT, The Proceedings of Metabolomics, Dec. 16, 2011, 6 pages.
Kimura et al., "The gut microbiota suppresses insulin-mediated fat accumulation via the short-chain fatty acid receptor GPR43." Nature Communications, 4:1829, May 7, 2013, 12 pages.
Kuwabara et al., "Altered metabolites in the plasma of autism spectrum disorder: a capillary electrophoresis time-of-flight mass spectroscopy study." Plos One, Sep. 2013, vol. 8, Issue No. 9, 8 pages.
Marcobal et al., "A metabolomic view of how the human gut microbiota impacts the host metabolome using humanized and gnotobiotic mice." The ISME Journal, Jun. 6, 2013, vol. 7, pp. 1933-1943.
Matsumoto et al., "Impact of Intestinal Microbiota on Intestinal Luminal Metabolome." Scientific Reports, Jan. 25, 2012, vol. 2, No. 233, 10 pages.
Notification of Transmittal of Translation of the International Preliminary Report on Patentability and International Preliminary Report on Patentability for International Application No. PCT/JP2016/004104 dated Mar. 22, 2018 by the International Bureau of WIPO, 12 pages.
Nakanishi, "Evaluation of the effects of prebiotics on murine gut microbial ecology by multi-omic based network analysis." Grants-in-Aid for Scientific Research Kenkyu Seika Hokokusho, Jun. 14, 2015, 5 pages, English abstract only.
Obana et al., "Effect of Dietary Fiber on Fecal and Urinary Excretion of Trp-P-2 in the Rat." Food Hyg. Saf. Sci., Oct. 1992, vol. 33, No. 5, pp. 437-441.
Romick-Rosendale, et al., "NMR-based metabonomics analysis of mouse urine ad fecal extracts following oral treatment with the broad-spectrum antibiotic enrofloxacin (Baytril)." Magnetic Resonanc in Chemistry, Sep. 18, 2009, vol. 47, pp. S36-S46.
Sato et al., "Comparison of extraction methods of steroid hormones in feces." The Proceedings of Nihon University Faculty of Dentistry, 2007, vol. 35, pp. 49-56, English translation of Abstract only, 8 pages.
Turnbaugh et al., "An obesity-associated gut microbiome with increased capacity for energy harvest." Nature, vol. 444(7122), Dec. 2006, pp. 1027-1031.
Ujiie, et al., "Study on extraction of multiresidue pesticide analysis in fruit and vegetables." Annual Report of Miyagi Prefectural Institute of Public Health and Environment, 2007, No. 25, pp. 58-61.
Van Nood et al., "Duodenal Infusion of Donor Feces for Recurrent *Clostridium difficile*." The New England Journal of Medicine, vol. 368, No. 5, Jan. 31, 2013, pp. 407-415.
Vijay-Kumar et al., "Metabolic Syndrome and Altered Gut Microbiota in Mice Lacking Toll-Like Receptor 5." Science, vol. 328, Apr. 9, 2010, pp. 228-231, 5 pages. Downloaded from http://science.sciencemag.org on Apr. 19, 2018.
Wang et al., "Evaluation and optimization of sample preparation methods for metabolic profiling analysis of *Escherichia coli*." Electrophoresis 2015, 36, pp. 2140-2147.
Yoshimoto et al., "Obesity-induced gut microbial metabolite promotes liver cancer through senescence secretome." Nature, 2013, 8 pages.
Martin Iain Bahl, FEMS Microbiol Letter, vol. 329, 2012, pp. 193-197.
Michael Reck et al., "Stool Metatransriptomics: A Technical Guideline for mRNA Stabilisation and Isloation," BMC Genomics, Biomed Central, vol. 16,, No. 1, 18 pages, Jul. 4, 2015.

* cited by examiner

[Figure 1]
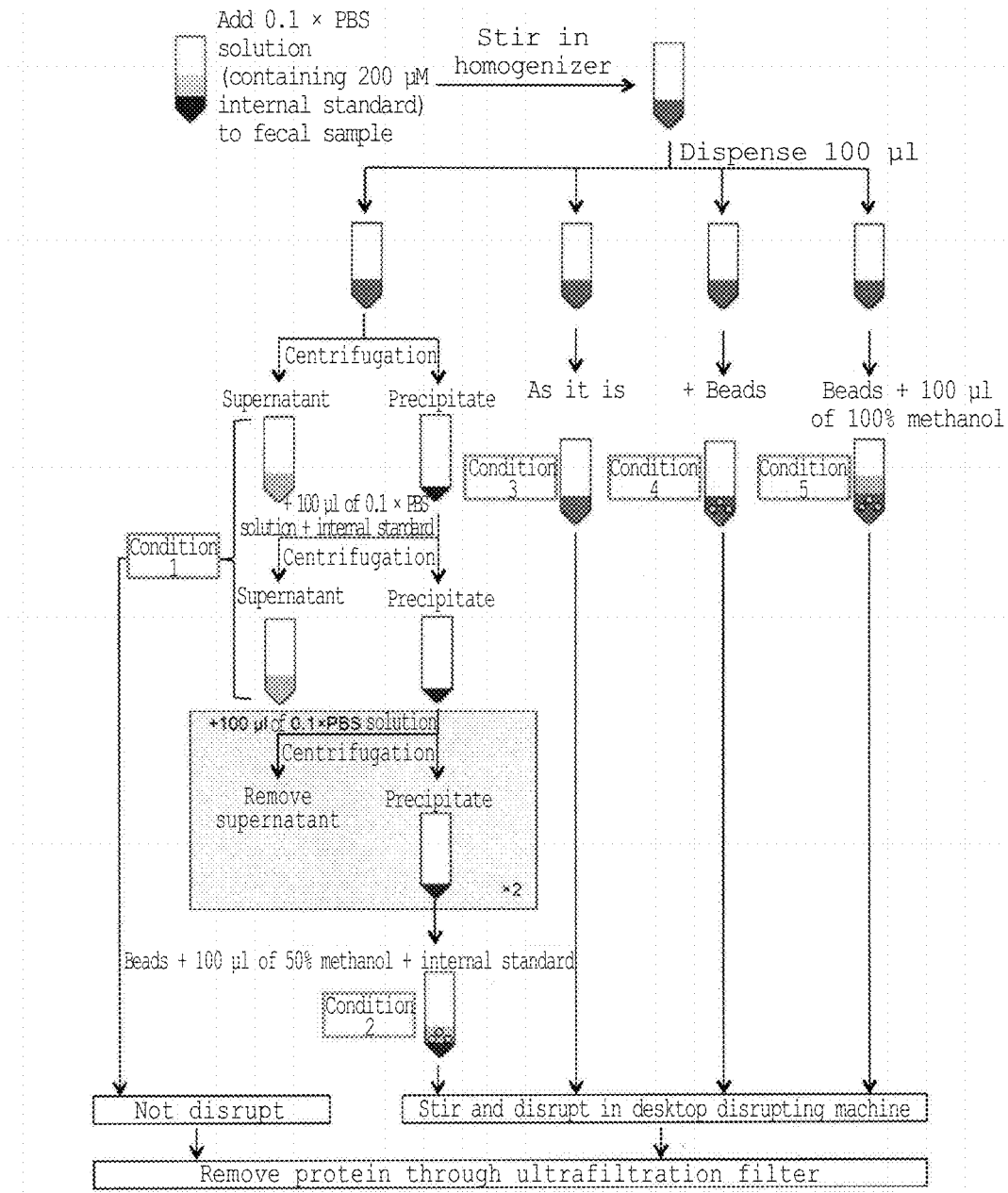

[Figure 2]
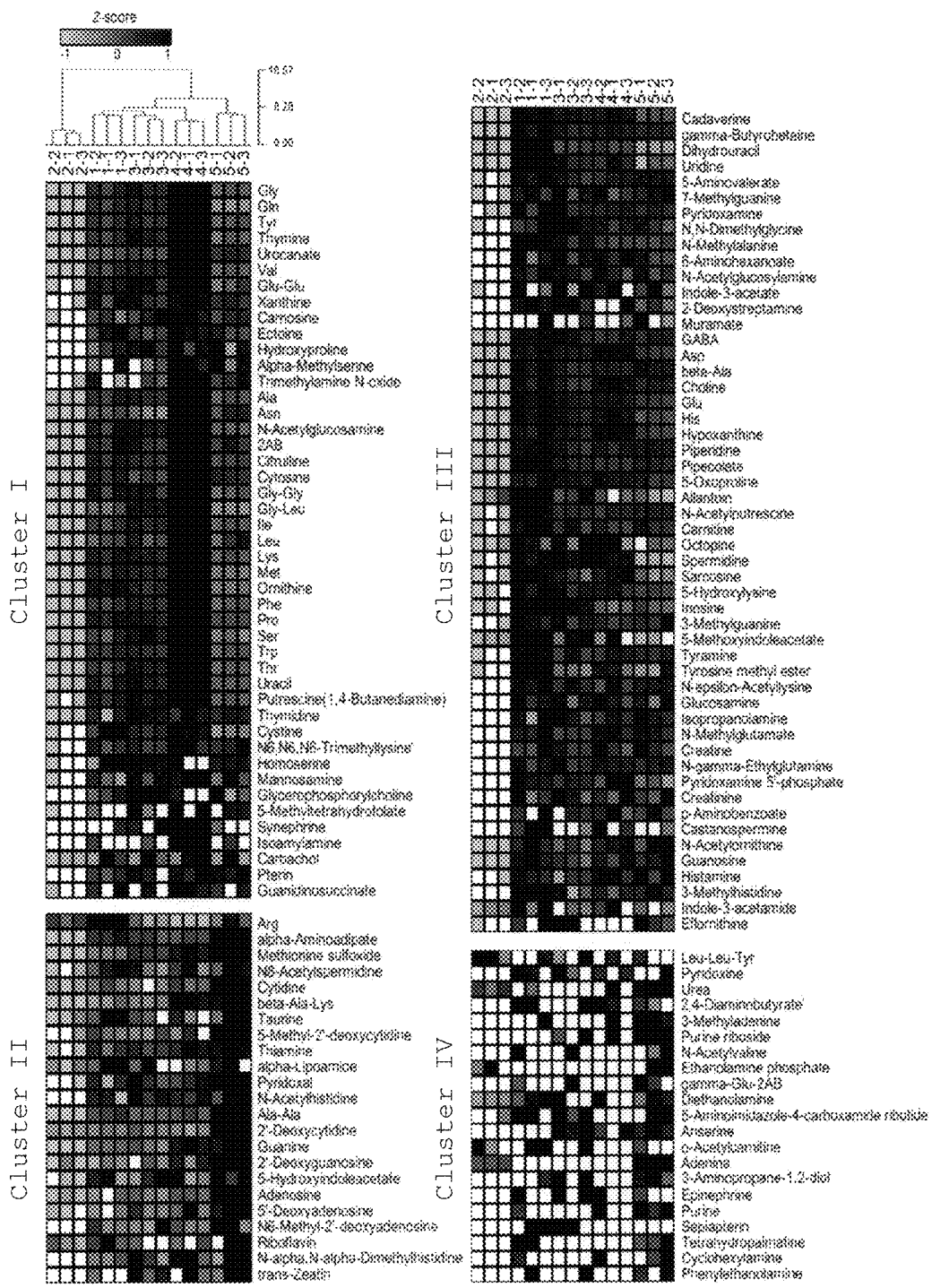

[Figure 3]
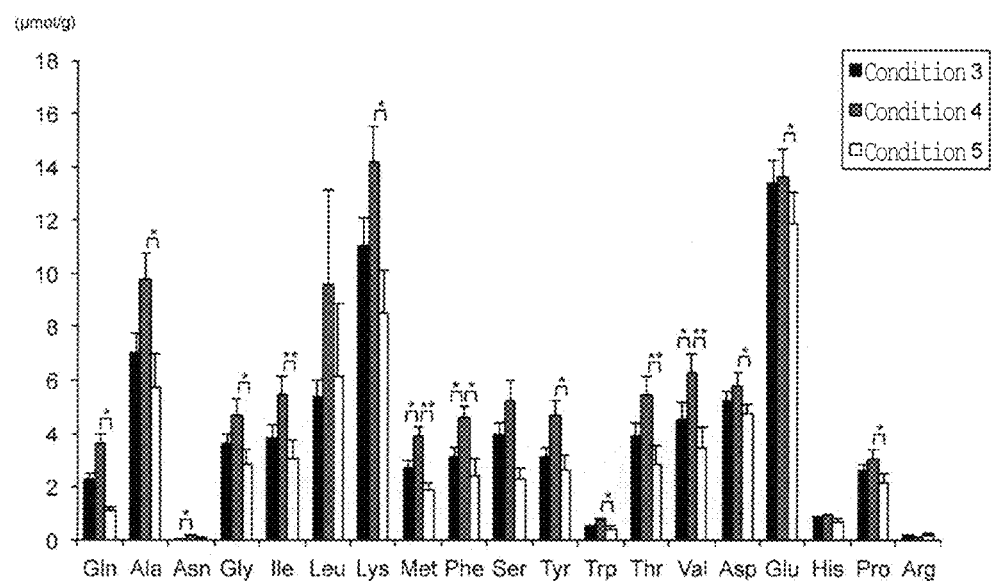
[Figure 4]
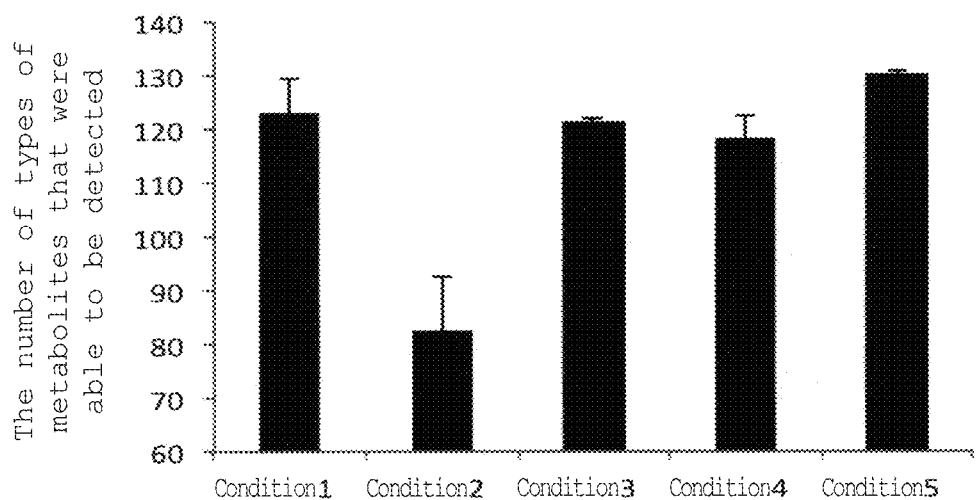

[Figure 5]
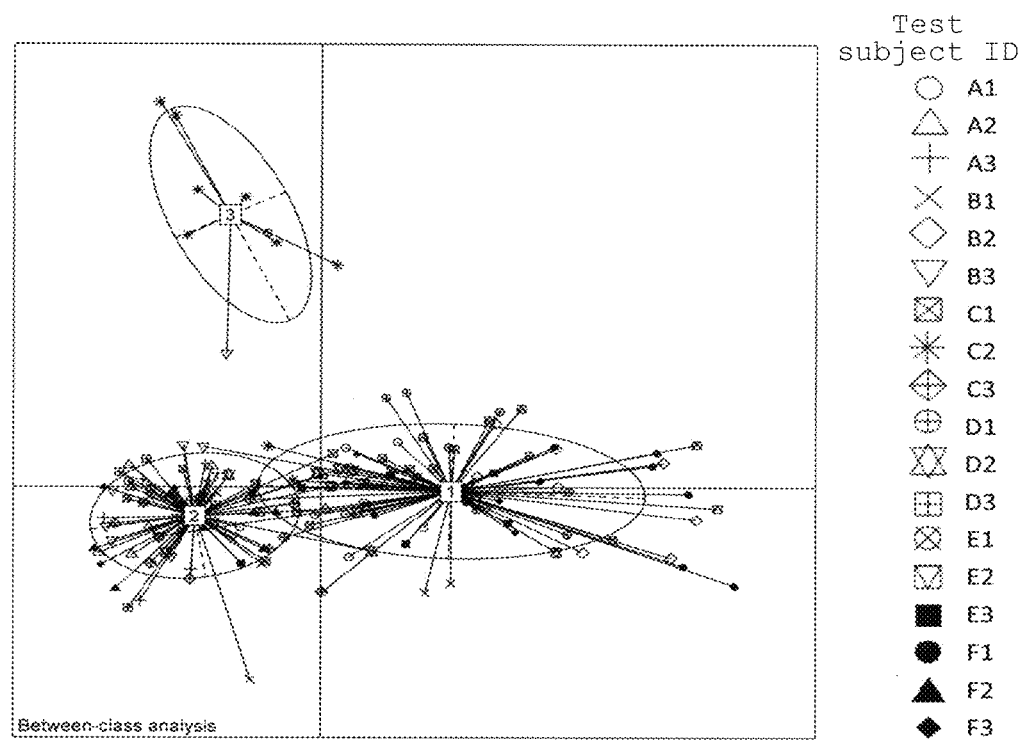

[Figure 6]
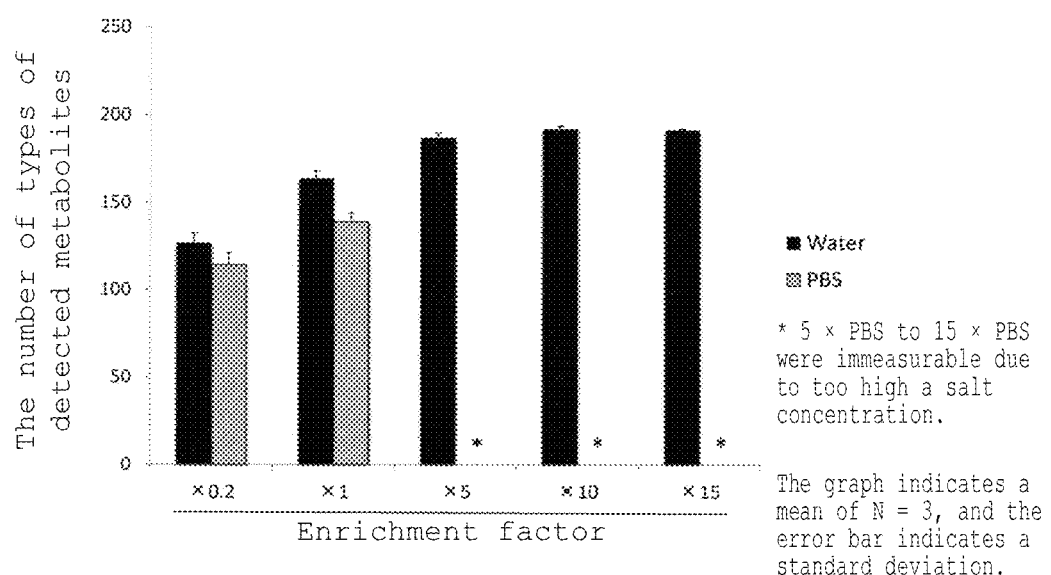

[Figure 7]
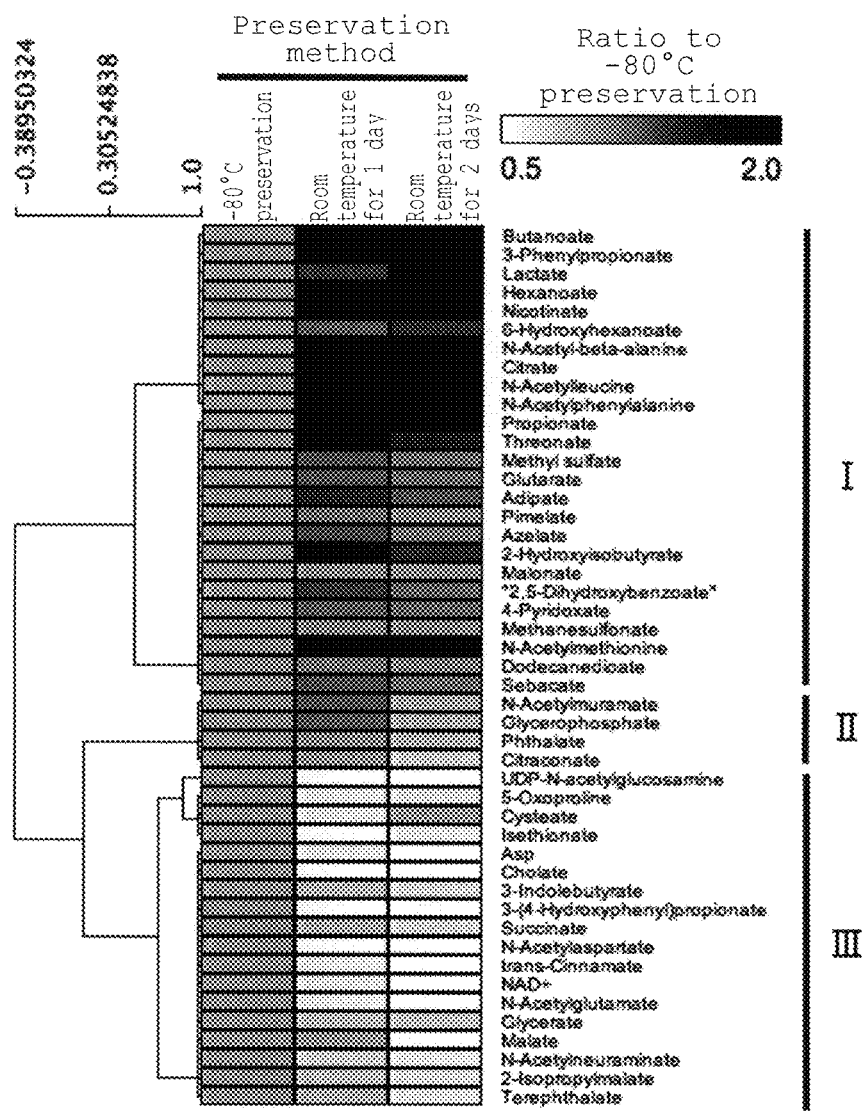

[Figure 8]
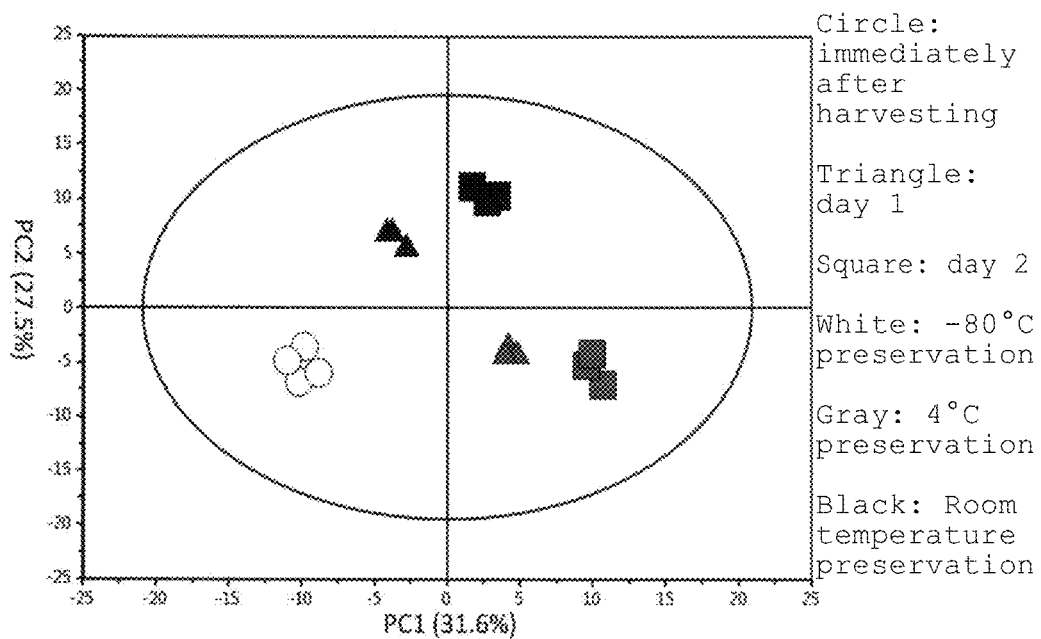

[Figure 9]
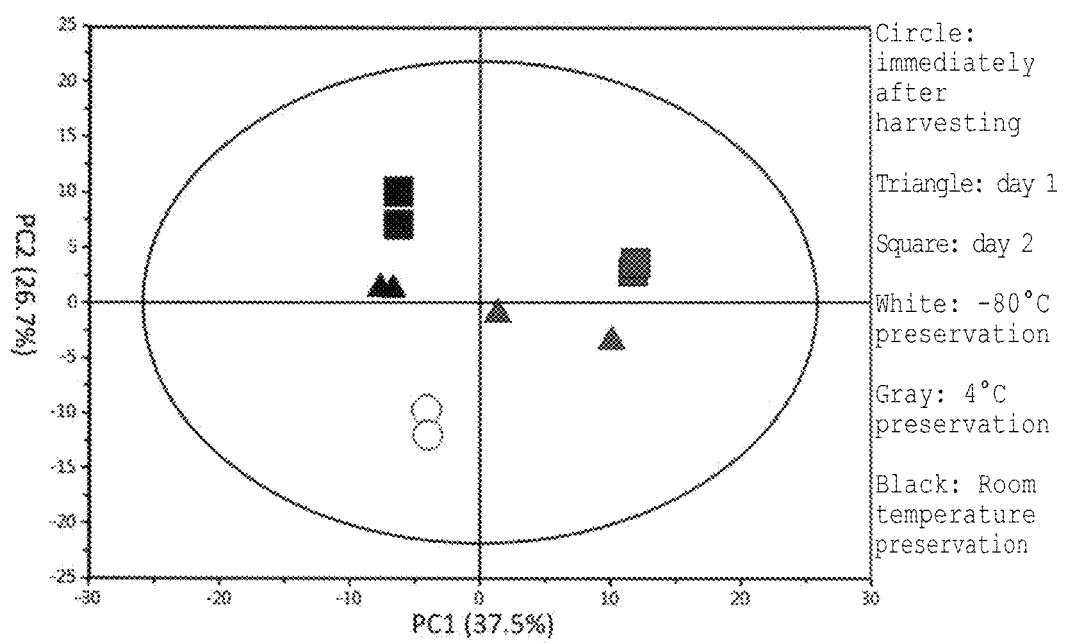

[Figure 10]
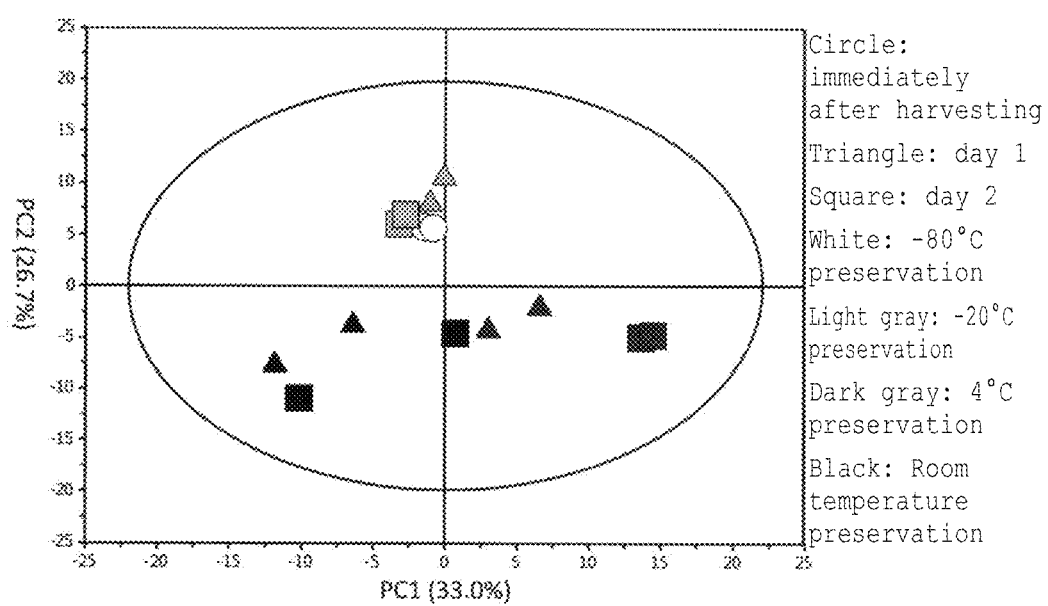

[Figure 11]
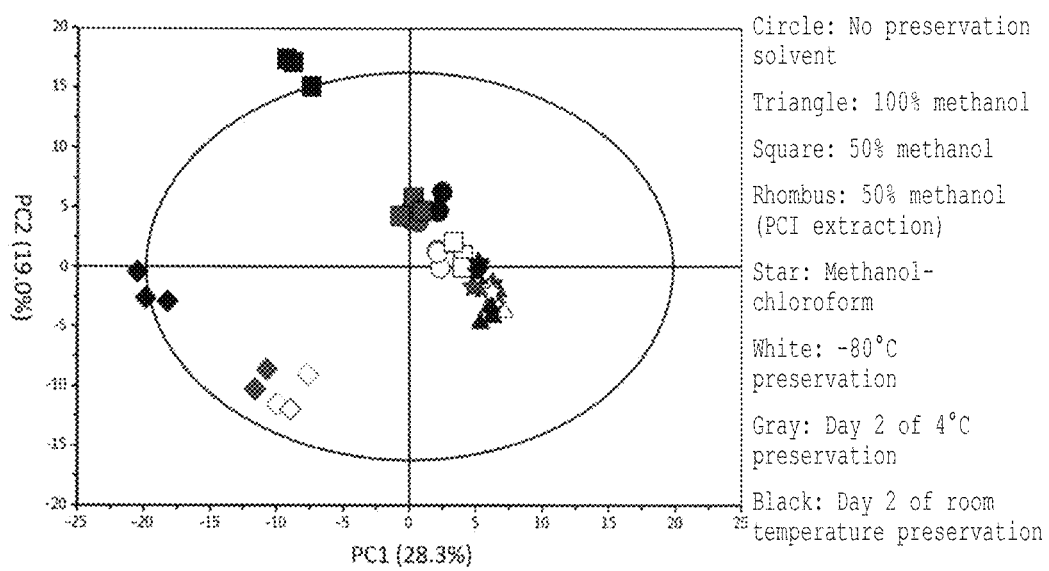

[Figure 12]
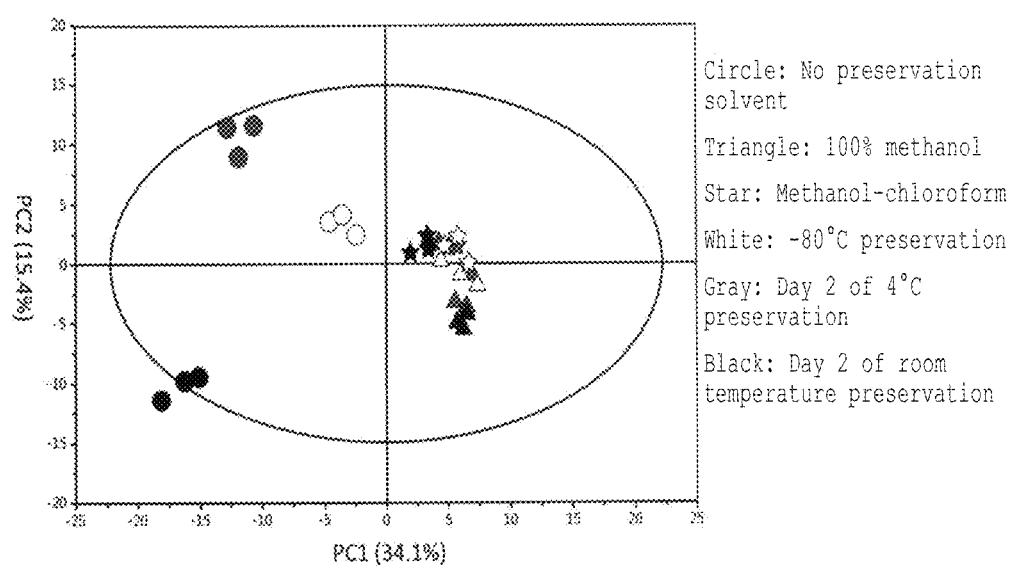

METHOD FOR EXTRACTING SUBSTANCE FROM FECES SAMPLE

CROSS REFERENCE TO RELATED APPLICATIONS

This application is a National Phase under 35 USC 371 of International Application No. PCT/JP2016/004104 filed on Sep. 8, 2016, which claims priority to Japanese Application No. 2015-179076 filed Sep. 11, 2016, the contents of which are hereby incorporated by reference in their entirety.

TECHNICAL FIELD

The present invention relates to a method for extracting substances from a fecal sample. Especially, the present invention relates to, for example, a method for extracting substances from a fecal sample, the method being suitable for conducting analyses such as metabolomic analysis using mass spectrometry or nuclear magnetic resonance spectrometry, and metagenomic analysis using a next-generation sequencer.

BACKGROUND ART

Over several hundred types of intestinal bacteria reside in the human intestinal tracts, and the total weight of the intestinal bacteria that reside in the intestines is approximately 1.5 kg per human. This community of the intestinal bacteria in the intestines is called intestinal microbiota. The intestinal microbiota is responsible for the degradation of non-digestible polysaccharides, the production of essential nutrient vitamins and the like, the construction of the immune system, the suppression of the growth of pathogenic microbes, etc. and is important for sustaining human homeostasis. On the other hand, it is suggested that the imbalance of the intestinal microbiota leads to various bowel diseases including colorectal cancer (non-patent documents 1 and 2), metabolic diseases such as type 2 diabetes mellitus (non-patent document 3), the onset of obesity (non-patent document 4), etc. Thus, the intestinal microbiota may have both positive and negative effects on human bodies.

In recent years, it has been reported that fecal transplantation therapy which involves transplanting fecal suspensions from healthy humans to *Clostridium difficile* colitis (pseudomembranous colitis) patients produced a higher therapeutic effect than that of treatment using antibiotics, indicating the potential of disease treatment by improvement in intestinal microbiota or intestinal environment (non-patent document 5). Thus, the association of the intestinal microbiota with our health has been pointed out. However, much remains unknown about the mechanism under which the intestinal microbiota influences human bodies. In recent years, the physiological functions of the intestinal microbiota have become clear as a result of gaining information on the organization or genes of the intestinal microbiota by the metagenomic analysis or metatranscriptomic analysis of the intestinal microbiota. However, the detailed physiological functions of the intestinal microbiota may need to be discussed in consideration of not only the functions of these genes but information on intestinal metabolites resulting from events between a host and the intestinal bacteria. Therefore, metabolome study on intestinal metabolites has received attention in recent years. The intestinal metabolites are produced as a result of metabolism by both a host and the intestinal bacteria and further utilized commonly by the intestinal bacteria and the host. Meanwhile, various previous studies have also gradually revealed that metabolites specific for the intestinal bacteria influence the biological response of the host. For example, butyrate produced from the intestinal microbiota has been reported to induce regulatory T-cell differentiation in a host and relieve inflammation in the intestinal tracts (non-patent document 6). Also, short-chain fatty acids including acetic acid have been reported to activate systemic energy metabolism and prevent obesity (non-patent document 7). Meanwhile, secondary bile acid produced through the degradation of primary bile acid by the intestinal bacteria has been reported to promote the onset of liver cancer (non-patent document 8). Thus, the metabolites produced from the intestinal microbiota have both positive and negative functions. The metabolomic analysis of the intestinal metabolites is considered to be useful in the "elucidation of a mechanism underlying host-intestinal microbiota interaction", "search for a novel functional substance in metabolites produced from intestinal microbiota", the "evaluation of an intestinal environment on the basis of intestinal metabolite profiles", etc.

Non-patent document 9 describes a method for measuring metabolites by dissolving mouse feces in a phosphate buffered saline (PBS) solution and measuring the supernatant by capillary electrophoresis time-of-flight mass spectrometry (CE-TOFMS). However, there are only a few study reports on the intestinal metabolites, and any approach of measuring the intestinal metabolites has not yet been established.

Methods using methanol or chloroform for deactivating metabolic enzymes are known as general methods for extracting metabolites from a sample such as animal cells or blood, not fecal samples. For example, a method for extracting metabolites using methanol or a water/methanol mixed solvent (non-patent document 10) and a method for extracting metabolites by liquid-liquid distribution using a chloroform/methanol mixed solvent (non-patent document 11) are often used. Patent document 1 describes a method for extracting metabolites from cells in the presence of methanol, chloroform, and water. In the case of extracting metabolites from cells having cell walls, such as bacterial or plant cells, a method is used which involves physically disrupting the cells using zirconia beads or the like, followed by extraction with a solvent such as methanol (non-patent document 12).

PRIOR ART DOCUMENTS

Patent Document

Patent document 1: Japanese unexamined Patent Application Publication No. 2008-005778

Non-Patent Documents

Non-patent document 1: Arthur, J. C., et al., "Intestinal inflammation targets cancer-inducing activity of the microbiota." Science; 338 (6103), 2012, pp. 120-123.
Non-patent document 2: Garrett, W. S., et al., "Communicable ulcerative colitis induced by T-bet deficiency in the innate immune system." Cell; 131 (1), 2007, pp. 33-45.
Non-patent document 3: Vijay-Kumar, M., et al., "Metabolic syndrome and altered gut microbiota in mice lacking Toll-like receptor 5." Science; 328 (5975), 2010, pp. 228-231. Non-patent document 4: Turnbaugh, P. J., et al., "An obesity-associated gut macrobiote with increased capacity for energy harvest." Nature; 444 (7122), 2006, pp. 1027-1031.

Non-patent document 5: van Nood, E., et al., "Duodenal infusion of donor feces for recurrent *Clostridium difficile*." The New England Journal of Medicine; 368 (5), 2013, pp. 407-415.

Non-patent document 6: Furusawa, Y., et al., "Commensal microbe-derived butyrate induces the differentiation of colonic regulatory T cells." Nature; 504 (7480), 2013, pp. 446-450.

Non-patent document 7: Kimura, I., et al., "The gut microbiota suppresses insulin-mediated fat accumulation via the short-chain fatty acid receptor GPR43." Nature Communications 2013; 4: 1829.

Non-patent document 8: Yoshimoto, S., et al., "Obesity-induced gut microbial metabolite promotes liver cancer through senescence secretome." Nature; 499 (7456), 2013, pp. 97-101.

Non-patent document 9: Matsumoto, M., et al., "Impact of intestinal microbiota on intestinal luminal metabolome." Scientific Reports 2012; 2: 233.

Non-patent document 10: Dietmair, S., et al., "Towards quantitative metabolomics of mammalian cells: development of a metabolite extraction protocol." Analytical Biochemistry; 404 (2), 2010, pp. 155-164.

Non-patent document 11: Kuwabara, H., et al., "Altered metabolites in the plasma of autism spectrum disorder: a capillary electrophoresis time-of-flight mass spectroscopy study." PLoS One 2013; 8 (9): e73814.

Non-patent document 12: Wang, X., et al., "Evaluation and optimization of sample preparation methods for metabolic profiling analysis of *Escherichia coli*." Electrophoresis 2015.

SUMMARY OF THE INVENTION

Object to be Solved by the Invention

An object of the present invention is to provide a more practical method for extracting substances from a fecal sample. More specifically, an object of the present invention is to provide a method for extracting substances from a fecal sample, the method being suitable for conducting analyses such as metabolomic analysis using mass spectrometry or nuclear magnetic resonance spectrometry, and metagenomic analysis using a next-generation sequencer.

Means to Solve the Object

The present inventors have conducted diligent studies to attain the objects and consequently completed the present invention by finding that the objects can be attained by a method for extracting one or more substances from a fecal sample, comprising:

(A) step A of suspending the fecal sample in any one of the following solvents (a) to (g) to obtain a suspension:

(a) a solvent comprising an aqueous solvent and a hydrophilic organic solvent;

(b) a solvent comprising an aqueous solvent and a hydrophobic organic solvent;

(c) a solvent comprising an aqueous solvent, a hydrophilic organic solvent and a hydrophobic organic solvent;

(d) a solvent comprising a hydrophilic organic solvent;

(e) a solvent comprising a hydrophobic organic solvent;

(f) a solvent comprising a hydrophilic organic solvent and a hydrophobic organic solvent; and (g) a solvent consisting of water;

(B) step B of separating a liquid layer comprising the solvent from the suspension; and (C) step C of removing proteins from the liquid layer and then obtaining the one or more substances.

The present inventors have also found that more types of substances can be extracted by combined use of an aqueous solvent with a hydrophilic organic solvent and/or a hydrophobic organic solvent. The present inventors have further found that metabolites such as amino acids can be more efficiently extracted by disruption and suspending treatment using beads in suspending the fecal sample in the solvent. Furthermore, the present inventors have separated the substances extracted from the fecal sample by capillary electrophoresis or chromatography, conducted mass spectrometry and/or nuclear magnetic resonance spectrometry to identify the one or more substances and to measure the concentrations of the one or more substances, and conducted cluster analysis on the measurement data. As a result, the present inventors have found that each characteristic substance in substance profiles can be classified into a cluster (group). The present inventors have further gained these and other findings and completed the present invention.

Furthermore, the present inventors have compared water and a PBS solution used as aqueous solvents and consequently found that more types of metabolites can be detected by using water. In the case of using a PBS solution, the present inventors have also found that when a sample is enriched and subjected to mass spectrometry, current flows excessively due to the influence of a salt concentration so that accurate measurement cannot be performed. The present inventors have further gained these and other findings and completed the present invention.

Moreover, in the case of preserving a fecal sample without being frozen after harvesting of the fecal sample and before extraction of substances from the fecal sample, the present inventors have found that, when the fecal sample is preserved in any one of solvents (h) and (i) given below, variations in metabolite profiles in the fecal sample during the preservation are suppressed. On the basis of these findings, the present invention has been completed.

(h) A solvent comprising an aqueous solvent and a hydrophilic organic solvent having a high concentration (e.g., 75% by weight or higher); and (i) a solvent comprising an aqueous solvent, a hydrophilic organic solvent and a hydrophobic organic solvent.

Specifically, the present invention relates to:

(1) a method for extracting one or more substances from a fecal sample, comprising:

step A of suspending the fecal sample in any one of the following solvents (a) to (g) to obtain a suspension:

(a) a solvent comprising an aqueous solvent and a hydrophilic organic solvent;

(b) a solvent comprising an aqueous solvent and a hydrophobic organic solvent;

(c) a solvent comprising an aqueous solvent, a hydrophilic organic solvent and a hydrophobic organic solvent;

(d) a solvent comprising a hydrophilic organic solvent;

(e) a solvent comprising a hydrophobic organic solvent;

(f) a solvent comprising a hydrophilic organic solvent and a hydrophobic organic solvent; and (g) a solvent consisting of water;

step B of separating a liquid layer comprising the solvent from the suspension; and step C of removing proteins from the liquid layer and then obtaining the one or more substances;

(2) the method for extracting one or more substances according to (1), wherein the step A is step A-1 of subjecting the fecal sample to disruption and suspending treatment with beads in any one of the solvents (a) to (a) to obtain a suspension;

(3) the method for extracting one or more substances according to (1) or (2), wherein the solvent comprises an aqueous solvent and a hydrophilic organic solvent, and a content of water in the solvent is in a range of 10 to 50% by weight;

(4) the method for extracting one or more substances according to (2) or (3), wherein a diameter of the beads in the step A-1 is in a range of 0.02 to 0.5 mm;

(5) the method for extracting one or more substances according to any one of (1) to (4), further comprising, before the step A or the step A-1, step X of subjecting a dried fecal sample to disruption treatment with beads to obtain dried fecal small pieces, wherein the dried fecal small pieces are used as the fecal sample of the step A or the step A-1;

(6) the method for extracting one or more substances according to (5), wherein a diameter of the beads in the step X is in a range of 0.6 to 15 mm;

(7) the method for extracting one or more substances according to any one of (3) to (6), wherein the solvent further comprises a hydrophobic organic solvent;

(8) the method for extracting one or more substances according to any one of (1) to (4) and (7), further comprising, before the step A or the step A-1, step Y of preserving a harvested fecal sample in the following solvent (h) or (i), wherein the fecal sample thus preserved in the step Y is used as the fecal sample of the step A or the step A-1:

(h) a solvent comprising an aqueous solvent and 75% by weight or more of a hydrophilic organic solvent; and (i) a solvent comprising an aqueous solvent, a hydrophilic organic solvent and a hydrophobic organic solvent;

(9) the method for extracting one or more substances according to any one of (1) to (8), wherein the aqueous solvent is selected from the group consisting of water, an aqueous solution of salt, and an aqueous buffer solution;

(10) the method for extracting one or more substances according to any one of (1) to (9), wherein the hydrophilic organic solvent is one or more solvents selected from the group consisting of methanol, ethanol, propanol, isopropanol, butanol, isobutanol, acetonitrile, dimethyl sulfoxide, dimethylformamide, dimethylacetamide, acetone, tetrahydrofuran and diethylene glycol; and

(11) the method for extracting one or more substances according to any one of (1) to (10), wherein the hydrophobic organic solvent is one or more solvents selected from the group consisting of chloroform, hexane, ether, diethyl ether, benzene, phenol, and isoamyl alcohol.

The present invention also relates to:

(12) a method for identifying one or more substances in a fecal sample, and measuring a concentration, composition or proportion of the one or more substances, comprising:

step P of separating the one or more substances extracted by the method according to any one of (1) to (11) by chromatography or capillary electrophoresis, and conducting mass spectrometry and/or nuclear magnetic resonance spectrometry to identify the one or more substances and to measure the concentration, composition or proportion of the one or more substances;

(13) a method for classifying a plurality of subjects into two or more clusters, comprising:

step Q of conducting the method according to (12) on each of fecal samples obtained from the plurality of subjects to identify two or more substances and to measure a concentration, composition or proportion of the two or more substances; and step S of conducting cluster analysis on data of the concentration, composition or proportion of the two or more substances obtained in the step Q, and classifying the plurality of subjects into two or more clusters according to similarity of substance profiles; and

(14) the method according to (13), further comprising, between the step Q and the step S, step R of standardizing the data of the concentration, composition or proportion of the two or more substances obtained in the step Q, wherein the data standardized in the step R is used in the cluster analysis in the step S.

Effect of the Invention

According to the present invention, one or more substances (preferably, intestinal metabolites) can be efficiently extracted from a fecal sample. According to the present invention, more types of substances can be extracted from a fecal sample. Accordingly, the present invention can provide a method for extracting substances from a fecal sample, the method being suitable for conducting analyses such as metabolomic analysis using mass spectrometry or nuclear magnetic resonance spectrometry, and metagenomic analysis using a next-generation sequencer.

BRIEF DESCRIPTION OF DRAWINGS

FIG. 1 is a diagram showing a flow chart of a method for extracting metabolites.

FIG. 2 is a diagram showing profiles of (cationic) metabolites detected in extraction samples 1 to 5. The hierarchical clustering of samples and metabolites was conducted using Pearson correlation coefficient. In the strings described above the heat maps, the letters before the hyphens represent the types of the extraction samples (extraction samples 1 to 5), and the numbers after the hyphens represent difference in the feces used. The heat maps depict the Z-score of each metabolite. The black depicts a high concentration, the light gray depicts a low concentration, and the white depicts a level equal to or less than the detection limit.

FIG. 3 is a diagram showing results of comparing the concentrations of 19 amino acids (glutamine [Gln], alanine [Ala], asparagine [Asn], glycine [Gly], isoleucine [Ile], leucine [Leu], lysine [Lys], methionine [Met], phenylalanine [Phe], serine [Ser], tyrosine [Tyr], tryptophan [Trp], threonine [Thr], valine [Val], aspartic acid [Asp], glutamic acid [Glu], histidine [His], proline [Pro], and arginine [Arg]) detected in extraction samples 3 to 5. In the graph, 3 bars for each amino acid depicts the concentrations (mean±standard deviation, [n=3]) of the amino acid detected in the extraction samples 3, 4, and 5 (conditions 3, 4, and 5) in order from the left.

FIG. 4 is a diagram showing results of comparing the numbers of metabolites detected in extraction samples 1 to 5. The ordinate depicts the number of types of metabolites detected under each extraction condition (mean±standard deviation, [n=3]), and the abscissa depicts each extraction condition.

FIG. 5 is a diagram showing results of conducting PAM (partitioning around medoids) clustering using metabolites detected in extraction sample Me and extraction sample MeCr. In the diagram, [1] to [3] depict butyrate, cholate and thiamine, respectively, and the ellipses centered around [1] to [3] depict a butyrate group, a cholate group and a thiamine group, respectively.

FIG. 6 is a diagram showing results of comparing the number of detected metabolites among the varying enrichment factors of a PBS solution or water extraction sample. The ordinate depicts the number of types of metabolites detected under each extraction condition (mean±standard deviation, [n=3]), and the abscissa depicts the extraction conditions and the enrichment factors.

FIG. 7 is a diagram showing results of analyzing variations in metabolite profiles in the preservation of a fecal sample at room temperature for 1 to 2 days with respect to −80° C. preservation. In the diagram, "I" depicts metabolites that exhibited increase in concentration by the preservation of the fecal sample at room temperature for 1 to 2 days. "II" depicts metabolites that exhibited increase in concentration by the preservation of the fecal sample at room temperature for 1 day and decrease in concentration by the preservation at room temperature for 2 days. "III" depicts metabolites that exhibited decrease in concentration by the preservation of the fecal sample at room temperature for 1 to 2 days.

FIG. 8 is a diagram showing results of extracting metabolites by a methanol-chloroform method from a fecal sample preserved at −80° C. immediately after feces sampling or preserved at room temperature or 4° C. for 1 to 2 days, and conducting principal component analysis using the detected metabolites.

FIG. 9 is a diagram showing results of extracting metabolites by a 50% methanol method from a fecal sample preserved at −80° C. immediately after feces sampling or preserved at room temperature or 4° C. for 1 to 2 days, and conducting principal component analysis using the detected metabolites.

FIG. 10 is a diagram showing results of extracting metabolites by a methanol-chloroform method from a fecal sample preserved at −80° C. immediately after feces sampling or preserved at room temperature, 4° C. or −20° C. for 1 to 2 days, and conducting principal component analysis using the detected metabolites.

FIG. 11 is a diagram showing results of preserving a fecal sample at room temperature, 4° C. or −80° C. for 2 days in each organic solvent (100% methanol [100% MeOH], 50% methanol [50% MeOH], or methanol-chloroform [MeOH/CHCl$_3$]) or in the absence of the organic solvent, and conducting principal component analysis using detected metabolites. The shapes of the plots depict the types of the organic solvents used in the preservation, and the colors depict the preservation temperatures.

FIG. 12 is a diagram showing results of conducting principal component analysis using the metabolites detected in the fecal sample preserved at room temperature, 4° C. or −80° C. for 2 days in 100% methanol [100% MeOH] or methanol-chloroform [MeOH/CHCl$_3$] or in the absence of the organic solvent in FIG. 11. The shapes of the plots depict the types of the organic solvents used in the preservation, and the colors depict the preservation temperatures.

MODE OF CARRYING OUT THE INVENTION

<Method for Extracting Substance from Fecal Sample>

The "method for extracting one or more substances from a fecal sample" of the present invention (hereinafter, also referred to as the "extraction method of the present invention") is not particularly limited as long the method is a method for extracting one or more substances from a fecal sample, comprising:

step A of suspending the fecal sample in any one of the following solvents (a) to (g) to obtain a suspension:

(a) a solvent comprising an aqueous solvent and a hydrophilic organic solvent;
(b) a solvent comprising an aqueous solvent and a hydrophobic organic solvent;
(c) a solvent comprising an aqueous solvent, a hydrophilic organic solvent and a hydrophobic organic solvent;
(d) a solvent comprising a hydrophilic organic solvent;
(e) a solvent comprising a hydrophobic organic solvent;
(f) a solvent comprising a hydrophilic organic solvent and a hydrophobic organic solvent; and
(g) a solvent consisting of water;

step B of separating a liquid layer comprising the solvent from the suspension; and step C of removing proteins from the liquid layer and then obtaining the one or more substances.

(Fecal Sample)

Examples of the organism species from which the "fecal sample" according to the present invention is derived include, but are not particularly limited to, a mammal such as a human, a mouse, a rat, cattle, sheep, a horse, and a monkey. Among them, a human is preferred.

(Substance)

The "substance" according to the present invention is not particularly limited as long as the substance is contained in the fecal sample. Examples thereof include a hydrophilic substance, a lipophilic substance, and an amphiphilic substance and more specifically include an acidic, neutral or basic hydrophilic substance, an acidic, neutral or basic lipophilic substance, and an acidic, neutral or basic amphiphilic substance. Preferred examples of the "substance" according to the present invention include: an intestinal metabolite; a nucleic acid such as DNA and RNA; a bile acid such as cholic acid and deoxycholic acid; a short-chain fatty acid such as acetic acid, propionic acid, and butyric acid; an organic acid such as lactic acid and succinic acid; an amino acid; a carbohydrate such as a monosaccharide, a disaccharide, and a trisaccharide; an uremic toxin such as indoxyl sulfate; and a lipid such as a fatty acid and a neutral fat.

The "intestinal metabolite" in the present specification is a substance produced by synthesis and/or degradation based on a substance incorporated from the outside world by the organism (host) from which the fecal sample is derived and/or intestinal microbiota, and means a substance that exists or has existed in the intestines (preferably, the large intestine) of the host. Examples of the intestinal metabolite specifically include: a short-chain fatty acid having 2 to 6 carbon atoms; an amino acid; a vitamin; a polyamine; a nucleic acid; a bile acid; a carbohydrate; and a uremic toxin, and preferably include a substance described in Tables 2 to 5 mentioned later. The extraction method of the present invention can more exhaustively extract intestinal metabolites from the fecal sample.

(Step A)

The step A in the extraction method of the present invention is not particularly limited as long as the step is of suspending the fecal sample in any one of the solvents (a) to (g) to obtain a suspension.

(Solvent)

Examples of the "aqueous solvent" in these solvents include: water such as purified water; an aqueous buffer solution; and an aqueous solution containing a pH adjuster. Water is preferred from the viewpoint of extracting more types of intestinal metabolites. In the case of performing extraction using an aqueous buffer solution containing a salt, and enriching the extract, followed by mass spectrometry, measurement might be impaired due to excessive current flow in the measurement. Therefore, water is more preferred than the aqueous buffer solution as the aqueous solvent. The pH of the aqueous buffer solution or the aqueous solution containing a pH adjuster can be appropriately set according to the properties, etc. of the one or more substances which are extraction targets, and can be, for example, in the range of pH 4 to 10 or in the range of pH 6 to 8. Examples of the aqueous buffer solution can include an aqueous phosphate buffer solution, an aqueous Tris-HCl buffer solution, and an aqueous Good's buffer solution. The aqueous solvent used may be commercially available or may be prepared using a reagent.

In the present specification, the "hydrophilic organic solvent" means an organic solvent having a solubility exceeding 20 g/100 g (20° C.) in water. The "hydrophilic organic solvent" is not particularly limited as long as it is a hydrophilic organic solvent. The hydrophilic organic solvent can be one or more solvents selected from the group consisting of methanol, ethanol, propanol, isopropanol, butanol, isobutanol, acetonitrile, dimethyl sulfoxide, dimethylformamide, dimethylacetamide, acetone, tetrahydrofuran and diethylene glycol, preferably one or more solvents selected from the group consisting of methanol, ethanol, propanol, isopropanol, acetonitrile, dimethyl sulfoxide, and acetone, more preferably methanol and/or ethanol, even more preferably methanol. The hydrophilic organic solvent used may be commercially available or may be prepared using a reagent.

In the present specification, the "hydrophobic organic solvent" means an organic solvent having a solubility of 20 g/100 g (20° C.) or lower in water. The "hydrophobic organic solvent" is not particularly limited as long as it is a hydrophobic organic solvent. The hydrophobic organic solvent can be one or more solvents selected from the group consisting of chloroform, hexane, ether, diethyl ether, benzene, phenol, and isoamyl alcohol, preferably one or more solvents selected from the group consisting of chloroform, hexane, and diethyl ether, more preferably chloroform and/or hexane. The hydrophobic organic solvent used may be commercially available or may be prepared using a reagent.

Examples of the solvents (a) to (f) can preferably include the following solvents (a1) to (f1) and can more preferably include the following solvents (a2) to (f2):
(a1) a solvent comprising an aqueous solvent and a hydrophilic organic solvent and comprising no hydrophobic organic solvent;
(b1) a solvent comprising an aqueous solvent and a hydrophobic organic solvent and comprising no hydrophilic organic solvent;
(c1) a solvent comprising an aqueous solvent, a hydrophilic organic solvent and a hydrophobic organic solvent;
(d1) a solvent comprising a hydrophilic organic solvent and comprising neither an aqueous solvent nor a hydrophobic organic solvent;
(e1) a solvent comprising a hydrophobic organic solvent and comprising neither an aqueous solvent nor a hydrophilic organic solvent; and
(f1) a solvent comprising a hydrophilic organic solvent and a hydrophobic organic solvent and comprising no aqueous solvent, and
(a2) a solvent consisting of an aqueous solvent and a hydrophilic organic solvent;
(b2) a solvent consisting of an aqueous solvent and a hydrophobic organic solvent;
(c2) a solvent consisting of an aqueous solvent, a hydrophilic organic solvent and a hydrophobic organic solvent;
(d2) a solvent consisting of a hydrophilic organic solvent;
(e2) a solvent consisting of a hydrophobic organic solvent; and
(f2) a solvent consisting of a hydrophilic organic solvent and a hydrophobic organic solvent.

The content of the aqueous solvent or the hydrophilic organic solvent in the solvents (a), (a1) and (a2) is not particularly limited and can be appropriately set according to the properties, etc. of the one or more substances which are extraction targets. In the solvents, for example, the content of the aqueous solvent can be in the range of 10 to 90% by weight, and the content of the hydrophilic organic solvent can be in the range of 90 to 10% by weight. In the solvents, preferably, the content of the aqueous solvent can be in the range of 10 to 50% by weight, and the content of the hydrophilic organic solvent can be in the range of 90 to 50% by weight. The weight ratio between the aqueous solvent and the hydrophilic organic solvent in the solvents (a), (a1) and (a2) is not particularly limited and can be appropriately set according to the properties, etc. of the one or more substances which are extraction targets. The weight ratio can be, for example, in the range of 1:9 to 9:1, preferably in the range of 1:9 to 5:1.

In a preferred aspect, the solvents (a), (a1) and (a2) can each be an aqueous methanol solution having a methanol concentration in the range of 10 to 90% by weight, preferably an aqueous methanol solution having a methanol concentration in the range of 10 to 50% by weight, more preferably an aqueous methanol solution having a methanol concentration of 50% by weight.

The content of the aqueous solvent or the hydrophobic organic solvent in the solvents (b), (b1) and (b2) is not particularly limited and can be appropriately set according to the properties, etc. of the one or more substances which are extraction targets. In the solvents, for example, the content of the aqueous solvent can be in the range of 10 to 90% by weight, and the content of the hydrophobic organic solvent can be in the range of 90 to 10% by weight. In the solvents, preferably, the content of the aqueous solvent can be in the range of 10 to 50% by weight, and the content of the hydrophobic organic solvent can be in the range of 90 to 50% by weight. The weight ratio between the aqueous solvent and the hydrophobic organic solvent in the solvents (b), (b1) and (b2) is not particularly limited and can be appropriately set according to the properties, etc. of the one or more substances which are extraction targets. The weight ratio can be, for example, in the range of 1:9 to 9:1, preferably in the range of 1:9 to 5:1.

The content of the aqueous solvent, the hydrophilic organic solvent or the hydrophobic organic solvent in the solvents (c), (c1) and (c2) is not particularly limited and can be appropriately set according to the properties, etc. of the one or more substances which are extraction targets. In the solvents, for example, the content of the aqueous solvent can be in the range of 5 to 85% by weight, the content of the hydrophilic organic solvent can be in the range of 5 to 85% by weight, and the content of the hydrophobic organic solvent can be in the range of 5 to 85% by weight. In the solvents, preferably, the content of the aqueous solvent can be in the range of 5 to 60% by weight, the content of the hydrophilic organic solvent can be in the range of 10 to 70% by weight, and the content of the hydrophobic organic solvent can be in the range of 10 to 70% by weight. In the solvents, more preferably, the content of the aqueous solvent can be in the range of 5 to 30% by weight, the content of the hydrophilic organic solvent can be in the range of 30 to 50% by weight, and the content of the hydrophobic organic solvent can be in the range of 30 to 50% by weight. The weight ratio between the aqueous solvent and the hydrophilic organic solvent, the weight ratio between the aqueous solvent and the hydrophobic organic solvent, or the weight ratio between the hydrophilic organic solvent and the hydrophobic organic solvent in the solvents (c), (c1) and (c2) is not particularly limited and can be appropriately set according to the properties, etc. of the one or more substances which are extraction targets. The weight ratio between the aqueous solvent and the hydrophilic organic solvent can be, for example, in the range of 1:9 to 9:1, preferably in the range of 1:9 to 4:6. The weight ratio between the aqueous solvent and the hydrophobic organic solvent can be, for example, in the range of 1:9 to 9:1, preferably in the range of 1:9 to 4:6. The weight ratio between the hydrophilic organic solvent and the hydrophobic organic solvent can be, for example, in the range of 1:9 to 9:1, in particular in the range of 3:7 to 7:3.

In a preferred aspect, the solvents (c), (c1) and (c2) can each be a solvent having a content of water in the range of 5 to 85% by weight, a content of methanol in range of 5 to 85% by weight, and a content of chloroform in the range of 5 to 85% by weight, preferably a solvent having a content of water in the range of 5 to 60% by weight, a content of methanol in the range of 10 to 70% by weight, and a content of chloroform in the range of 10 to 70% by weight, more preferably a solvent having a content of water in the range of 5 to 30% by weight, a content of methanol in the range of 30 to 50% by weight, and a content of chloroform in the range of 30 to 50% by weight.

The content of the hydrophilic organic solvent in the solvents (d) and (d1) is not particularly limited and can be appropriately set according to the properties, etc. of the one or more substances which are extraction targets. In the solvents, for example, the content of the hydrophilic organic solvent can be in the range of 80 to 100% by weight. In the solvents, preferably, the content of the hydrophilic organic solvent can be in the range of 95 to 100% by weight.

The content of the hydrophobic organic solvent in the solvents (e) and (e1) is not particularly limited and can be appropriately set according to the properties, etc. of the one or more substances which are extraction targets. In the solvents, for example, the content of the hydrophobic organic solvent can be in the range of 80 to 100% by weight. In the solvents, preferably, the content of the hydrophobic organic solvent can be in the range of 95 to 100% by weight.

The content of the hydrophilic organic solvent or the hydrophobic organic solvent in the solvents (f), (f1) and (f2) is not particularly limited and can be appropriately set according to the properties, etc. of the one or more substances which are extraction targets. In the solvents, for example, the content of the hydrophilic organic solvent can be in the range of 10 to 90% by weight, and the content of the hydrophobic organic solvent can be in the range of 90 to 10% by weight. In the solvents, preferably, the content of the hydrophilic organic solvent can be in the range of 30 to 70% by weight, and the content of the hydrophobic organic solvent can be in the range of 70 to 30% by weight. The weight ratio between the hydrophilic organic solvent and the hydrophobic organic solvent in the solvents (f), (f1) and (f2) is not particularly limited and can be appropriately set according to the properties, etc. of the one or more substances which are extraction targets. The weight ratio can be, for example, in the range of 1:9 to 9:1, preferably in the range of 3:7 to 7:3.

(Method for Suspending Fecal Sample in Solvent)

In suspending the fecal sample in any one of the solvents (a) to (g), the fecal sample may be suspended by the addition of the fecal sample into the solvent or may be suspended by the addition of the solvent to the fecal sample. Examples of the method for suspending the fecal sample into the solvent include, but are not particularly limited to, a method of suspending the fecal sample in the solvent by shaking and/or stirring the solvent and the fecal sample, and preferably include a method of suspending the fecal sample in the solvent by stirring the solvent and the fecal sample in a homogenizer of ultrasonic type, pressure type, or the like, and a method of suspending the fecal sample in the solvent by shaking and/or stirring the solvent and the fecal sample (preferably, a container containing them) in a vortex mixer. (Step A-1)

The step A is preferably the following step A-1 from the viewpoint of extracting more types of substances from the fecal sample or from the viewpoint of extracting more types of substances at higher concentrations from within intestinal microbiota in the fecal sample:

step A-1: step A-1 of subjecting the fecal sample to disruption and suspending treatment with beads in any one of the solvents (a) to (g) to obtain a suspension.

As also described in the paragraph "Background Art", in recent years, the physiological functions of intestinal microbiota have become clear as a result of gaining information on the organization or genes of the intestinal microbiota by the metagenomic analysis or metatranscriptomic analysis of the intestinal microbiota.

Meanwhile, more highly accurate metabolomic analysis can be conducted, provided that metabolite profiles, also including metabolites accumulated within intestinal microbiota, can be obtained by disruption treatment with beads. It is considered that the physiological functions of the intestinal microbiota can be elucidated in more detail by combining the results of this highly accurate metabolomic analysis with the gene information mentioned above.

In the step A-1, examples of the method for subjecting the fecal sample to disruption and suspending treatment with beads in the solvent to obtain a suspension include, but are not particularly limited to, a method of shaking and/or stirring the solvent, the fecal sample and beads in a state where the solvent, the fecal sample and the beads coexist, and thereby subjecting the fecal sample to disruption and suspending treatment with the beads to obtain a suspension, and preferably include a method of shaking and/or stirring the solvent, the fecal sample and the beads (preferably, a container containing them) in a cell disruption apparatus such as a vortex mixer or Shake Master NEO (manufactured by Bio-Medical Science Co., Ltd.) and thereby subjecting the fecal sample to disruption and suspending treatment with the beads to obtain a suspension.

The material for the beads in the step A-1 is not particularly limited as long as the fecal sample can be disrupted (preferably, microbes in the fecal sample can be disrupted). Examples thereof include zirconia (zirconium dioxide), zirconium, quartz, silica, stainless, magnesium oxide, titanium oxide, manganese oxide, magnesium, titanium, and manganese.

The shape of the beads in the step A-1 is not particularly limited as long as the fecal sample can be disrupted (preferably, microbes in the fecal sample can be disrupted). Examples thereof can include a substantially spherical shape and can preferably include a spherical shape.

The size of the beads in the step A-1 is not particularly limited as long as the fecal sample can be disrupted (preferably, microbes in the fecal sample can be disrupted). The length of the longest portion of the beads is, for example, in the range of 0.02 to 0.5 mm, preferably in the range of 0.05 to 0.3 mm. In the case of spherical beads, the diameter of the beads is in the range of 0.02 to 0.5 mm, preferably in the range of 0.05 to 0.3 mm.

The beads for use in the step A-1 can be commercially available.

The amount of the beads added in the step A-1 is not particularly limited as long as the fecal sample can be disrupted (preferably, microbes in the fecal sample can be disrupted). The amount of the beads added can be, for example, in the range of 1 mg to 1 g, preferably in the range of 10 to 800 mg, more preferably in the range of 40 to 600 mg, per mL of the solvent.

Beads listed as to step X mentioned later may be used in combination with the beads listed as to the step A-1, as the beads in the step A-1.

(Step X)

The extraction method of the present invention does not have to further have the following step X and preferably, further has the following step X before the step A or the step A-1 from the viewpoint that the respective amounts of fecal samples for use in extraction can be as equal as possible by obtaining dried fecal small pieces:

step X: step X of subjecting a dried fecal sample to disruption treatment with beads to obtain dried fecal small pieces.

When the extraction method of the present invention further has the step X, the dried fecal small pieces obtained in the step X are used as the fecal sample of the step A or the step A-1.

The material for the beads in the step X is not particularly limited as long as the fecal sample can be disrupted. Specifically, examples thereof can include the material listed as the material for the beads in the step A-1. The material for the beads in the step X is the same as or different from that for the beads in the step A-1.

The shape of the beads in the step X is not particularly limited as long as the fecal sample can be disrupted. Examples thereof can include a substantially spherical shape and can preferably include a spherical shape. The shape of the beads in the step X is the same as or different from that for the beads in the step A-1.

The size of the beads in the step X is not particularly limited as long as the fecal sample can be disrupted. The length of the longest portion of the beads is, for example, in the range of 0.6 to 15 mm, preferably in the range of 1.5 to 9 mm. In the case of spherical beads, the diameter of the beads is in the range of 0.6 to 15 mm, preferably in the range of 1.5 to 9 mm.

The beads for use in the step X can be commercially available.

The amount of the beads added in the step X is not particularly limited as long as the fecal sample can be disrupted. The amount of the beads added can be, for example, in the range of 1 mg to 1 g, preferably in the range of 50 to 500 mg, per 10 mg (based on a dry weight) of the fecal sample.

A preferred aspect of the step A or the step A-1 in the extraction method of the present invention differs depending on the characteristics of the substances which are extraction targets and can be selected according to the characteristics. In the case of extracting, for example, metabolites of cluster II in Examples mentioned later, it is preferred to perform the disruption treatment with beads as described in the step A-1, and it is also preferred to use an aqueous solvent in combination with a hydrophilic organic solvent as the solvent. On the other hand, in the case of extracting metabolites of cluster I in Examples mentioned later, it is preferred to perform the disruption treatment with beads as described in the step A-1, and it is also preferred to use an aqueous solvent alone without being used in combination with a hydrophilic organic solvent, as the solvent. In the case of extracting metabolites of cluster III in Examples mentioned later, there is little difference depending on whether or not to perform the disruption treatment with beads as described in the step A-1, and there is little difference depending whether an aqueous solvent is used alone or in combination with a hydrophilic organic solvent as the solvent.

(Step Y)

The extraction method of the present invention does not have to further have the following step Y and preferably, further has the following step Y before the step A or the step A-1 from the viewpoint of suppressing variations in metabolite profiles in a fecal sample during preservation in the case of preserving the fecal sample without being frozen after harvesting of the fecal sample and before extraction of substances from the fecal sample: step Y: step Y of preserving a harvested fecal sample in the following solvent (h) or (i):

(h) a solvent comprising an aqueous solvent and 75% by weight or more of a hydrophilic organic solvent; and (i) a solvent comprising an aqueous solvent, a hydrophilic organic solvent and a hydrophobic organic solvent.

When the extraction method of the present invention further has the step Y, the fecal sample thus preserved in the step Y is used as the fecal sample of the step A or the step A-1.

Examples and preferred examples of the "aqueous solvent", the "hydrophilic organic solvent" and the "hydrophobic organic solvent" in the solvent of the step Y can include those listed about the "aqueous solvent", the "hydrophilic organic solvent" and the "hydrophobic organic solvent", respectively, in the solvent of the step A. The "aqueous solvent", the "hydrophilic organic solvent" and the "hydrophobic organic solvent" for use in the solvent of the step Y are the same as or different from the "aqueous solvent", the "hydrophilic Organic Solvent" and the "hydrophobic organic solvent", respectively, for use in the solvent of the step A or the step A-1.

Examples of the solvent (h) or (i) can preferably include the following solvents (h1) and (i1) and can more preferably include the following solvents (h2) and (i2):

(h1) a solvent comprising an aqueous solvent and 75% by weight or more of a hydrophilic organic solvent and comprising no hydrophobic organic solvent;

(i1) a solvent comprising an aqueous solvent, a hydrophilic organic solvent and a hydrophobic organic solvent;

(h2) a solvent consisting of an aqueous solvent and 75% by weight or more of a hydrophilic organic solvent; and (i2) a solvent consisting of an aqueous solvent, a hydrophilic organic solvent and a hydrophobic organic solvent.

The solvent (h) is a solvent comprising an aqueous solvent and a hydrophilic organic solvent. In the solvent, the content of the hydrophilic organic solvent is 75% by weight or more. The content of the hydrophilic organic solvent in the solvents (h), (h1) and (h2) is not particularly limited as long as the content is 75% by weight or more. The content is preferably 80% by weight or more, more preferably 85% by weight or more, even more preferably 90% by weight or more, further preferably 95% by weight or more, still further preferably 98% by weight or more. The content of the aqueous solvent in the solvents (h), (h1) and (h2) is not particularly limited as long as the content is less than 25% by weight. The content of the aqueous solvent can be appropriately set according to the content of the hydrophilic organic solvent and is, for example, less than 20% by weight, less than 15% by weight, less than 10% by weight, less than 5% by weight, or less than 2% by weight. The weight ratio of the hydrophilic organic solvent to the aqueous solvent in the solvents (h), (h1) and (h2) is not particularly limited as long as the weight ratio is higher than 3-fold. The weight ratio can be higher than 3-fold and 100-fold or lower.

In a preferred aspect, the solvents (h), (h1) and (h2) can each be an aqueous methanol solution having a methanol concentration of 75% by weight or more (preferably 80% by weight or more, more preferably 85% by weight or more, even more preferably 90% by weight or more, further preferably 95% by weight or more, still further preferably 98% by weight or more) and less than 100% by weight, or 100% by weight of a methanol solution, more preferably 100% by weight of a methanol solution.

The content of the aqueous solvent, the hydrophilic organic solvent or the hydrophobic organic solvent in the solvents (i), (i1) and (i2) is not particularly limited and can be appropriately set. In the solvents, for example, the content of the aqueous solvent can be in the range of 1 to 40% by weight, the content of the hydrophilic organic solvent can be in the range of 10 to 95% by weight, and the content of the hydrophobic organic solvent can be in the range of 5 to 60% by weight. In the solvents, preferably, the content of the aqueous solvent can be in the range of 1 to 25% by weight, the content of the hydrophilic organic solvent can be in the range of 20 to 90% by weight, and the content of the hydrophobic organic solvent can be in the range of 10 to 50% by weight. In the solvents, more preferably, the content of the aqueous solvent can be in the range of 1 to 15% by weight, the content of the hydrophilic organic solvent can be in the range of 40 to 80% by weight, and the content of the hydrophobic organic solvent can be in the range of 15 to 45% by weight. The weight ratio between the aqueous solvent and the hydrophilic organic solvent, the weight ratio between the aqueous solvent and the hydrophobic organic solvent, or the weight ratio between the hydrophilic organic solvent and the hydrophobic organic solvent in the solvents (i), (i1) and (i2) is not particularly limited and can be appropriately set. The weight ratio between the aqueous solvent and the hydrophilic organic solvent can be, for example, in the range of 1:30 to 1:3, preferably in the range of 1:20 to 1:5. The weight ratio between the aqueous solvent and the hydrophobic organic solvent can be, for example, in the range of 1:15 to 1:1.5, preferably in the range of 1:10 to 1:2.5. The weight ratio between the hydrophilic organic solvent and the hydrophobic organic solvent can be in the range of, for example, 6:1 to 2:3, preferably in the range of 4:1 to 1:1.

In a preferred aspect, the solvents (i), (i1) and (i2) can each be, for example, a solvent having a content of water in the range of 1 to 40% by weight, a content of methanol in the range of 10 to 95% by weight, and a content of chloroform in the range of 5 to 60% by weight, preferably a solvent having a content of water in the range of 1 to 25% by weight, a content of methanol in the range of 20 to 90% by weight, and a content of chloroform in the range of 10 to 50% by weight, more preferably a solvent having a content of water in the range of 1 to 15% by weight, a content of methanol in the range of 40 to 80% by weight, and a content of chloroform in the range of 15 to 45% by weight.

In the step Y, the method for preserving the harvested fecal sample in the solvent (h) or (i) is not particularly limited as long as the method allows this fecal sample to be contained in the solvent (h) or (i). For example, the solvent (h) or (i) may be added to the fecal sample, or the fecal sample may be added to the solvent (h) or (i).

The preservation temperature in the step (Y) is not particularly limited and is preferably 40° C. or lower, more preferably 30° C. or lower, even more preferably 25° C. or lower, further preferably 20° C. or lower, still further preferably 15° C. or lower, still further preferably 10° C. or lower, still further preferably 5° C. or lower, still further preferably 0° C. or lower, still further preferably −5° C. or lower, still further preferably −15° C. or lower, still further preferably −20° C. or lower, still further preferably −40° C. or lower, still further preferably −60° C. or lower, still further preferably −80° C. or lower, from the viewpoint of suppressing variations in metabolite profiles in the fecal sample immediately after harvesting. On the other hand, even if the fecal sample cannot be preserved in a frozen state because freezing equipment or the like cannot be used, the preservation temperature is, for example, 0° C. or higher, 3° C. or higher, 4° C. or higher, 6° C. or higher, or 10° C. or higher, from the viewpoint of enjoying the greater significance of the present invention in suppressing variations in metabolite profiles in the fecal sample immediately after harvesting.

Examples of the preservation temperature range in the step (Y) more specifically include the range of −90 to 40° C., the range of −90 to 30° C., the range of −80 to 30° C., the range of −80 to 25° C., and the range of −60 to 20° C. Preferred examples of the preservation temperature range more specifically include the range of 0 to 40° C., the range of 0 to 3.0° C., the range of 0 to 25° C., the range of 0 to 20° C., the range of 0 to 15° C., the range of 0 to 10° C., the range of 0 to 5° C., the range of 3 to 25° C., the range of 3 to 20° C., the range of 3 to 15° C., the range of 3 to 10° C., the range of 3 to 5° C., the range of 4 to 25° C., the range of 4 to 20° C., the range of 4 to 15° C., the range of 4 to 10° C., the range of 4 to 5° C., the range of 6 to 25° C., the range of 6 to 20° C., the range of 6 to 15° C., and the range of 6 to 10° C., from the viewpoint of enjoying the greater significance of the present invention.

The preservation period in the step (Y) is not particularly limited and can be appropriately set according to the preservation temperature, etc. When the preservation temperature is, for example, lower than 0° C., the preservation period is, for example, in the range of 1 minute to 1 month, in the range of 20 minutes to 3 weeks, or in the range of 1 hour to 2 weeks. When the preservation temperature is 0° C. or higher, the preservation period is, for example, in the range of 1 minute to 7 days, in the range of 20 minutes to 3 days, or in the range of 1 hour to 2 days.

The fecal sample thus preserved in the step Y can be used as the fecal sample of the step A or the step A-1. The method for using the fecal sample thus preserved in the step Y as the fecal sample of the step A or the step A-1 is not particularly limited. A portion or the whole of the solvent used in the preservation in the step Y (hereinafter, also simply referred to as the "preservation solvent") may or may not be removed after the preservation of the step Y. It is preferred that the preservation solvent should not be removed, from the viewpoint of suppressing variations in metabolite profiles in the fecal sample immediately after harvesting.

When the preservation solvent is not removed after the preservation of the step Y and when the preservation solvent is any one of the extraction solvents (a) to (g), the preservation solvent may be used directly as the extraction solvent to perform the step A or the step A-1. When the preservation solvent is not removed after the preservation of the step Y, it is preferred to convert the preservation solvent to the extraction solvent by allowing the preservation solvent to contain one or more solvents selected from the group consisting of an aqueous solvent, a hydrophilic organic solvent and a hydrophobic organic solvent. For example, the preservation solvent (h) may be directly used as the extraction solvent (a). The composition, etc. of the preservation solvent may be changed, for example, by the addition of an aqueous solvent, a hydrophilic organic solvent, or the like to the preservation solvent, and the resulting solvent may be used as the extraction solvent (a). The composition, etc. of the preservation solvent may be changed, for example, by the addition of a hydrophobic organic solvent or the like to the preservation solvent, and the resulting solvent may be used as the extraction solvent (c). Also, the preservation solvent (i) may be directly used as the extraction solvent (c). The composition, etc. of the preservation solvent may be changed, for example, by the addition of an aqueous solvent, a hydrophilic organic solvent, a hydrophobic organic solvent, or the like, and the resulting solvent may be used as the extraction solvent (c).

(Step B)

The step B in the extraction method of the present invention is not particularly limited as long as the step is of separating a liquid layer comprising the solvent from the suspension obtained in the step A or the step A-1.

(Method for Separating Liquid Layer)

Examples of the method for separating the liquid layer from the suspension can preferably include, but are not particularly limited to, a method of centrifuging the suspension and separating the supernatant. The centrifugation of the suspension can be performed using a commercially available centrifugation apparatus.

(Step C)

The step C in the extraction method of the present invention is not particularly limited as long as the step is of removing proteins from the liquid layer separated in the step B and then obtaining the one or more substances.

(Method for Removing Protein from Liquid Layer)

Examples of the method for removing proteins from the liquid layer separated in the step B can preferably include, but are not particularly limited to, a method of removing proteins from the liquid layer using a filter such as an ultrafiltration filter or a reverse osmosis filter. The ultrafiltration filter or the reverse osmosis filter used can be commercially available.

The one or more substances extracted from the fecal sample are contained in the liquid obtained by removing proteins from the liquid layer. It is preferred to dry the liquid from the viewpoint of the preservative quality of the extracted substances. These dried substances can be supplemented with and dissolved in a solvent such as water again before use in mass spectrometry or nuclear magnetic resonance spectrometry. It is preferred to also add internal standard substances for mass spectrometry or nuclear magnetic resonance spectrometry in adding the solvent.

<Method for Identifying One or More Substances in Fecal Sample, and Measuring Concentration, Composition or Proportion of the One or More Substances>

The "method for identifying one or more substances in a fecal sample, and measuring concentration, composition or proportion of the one or more substances" of the present invention (hereinafter, also referred to as the "identification and measurement method of the present invention") is not particularly limited as long as the method comprises step P of separating the one or more substances extracted by the extraction method of the present invention, by chromatography or capillary electrophoresis, and conducting mass spectrometry and/or nuclear magnetic resonance spectrometry to identify the one or more substances and to measure the concentration, composition or proportion of the one or more substances. Examples of the "chromatography" in the step P include liquid chromatography and gas chromatography. Liquid chromatography is preferred. The separation of the substances by chromatography or capillary electrophoresis (CE) can be performed by a routine method using a commercially available chromatograph (apparatus for chromatography) or a capillary electrophoresis apparatus.

The mass spectrometry is a measurement method using a mass spectrometry apparatus capable of converting substances into gaseous ions (ionization) using an ion source, moving the ions in vacuum in an analysis chamber, and separating the ionized substances according to mass-to-charge ratios by use of electromagnetic force or on the basis of difference in time of flight, followed by detection.

The ionization method using an ion source can be appropriately selected from methods such as EI, CI, FD, FAB, MALDI, and ESI. The method for separating the ionized substances in an analysis chamber can be appropriately selected from separation methods such as magnetic sector, quadrupole, ion trap, time-of-flight (TOF), and Fourier transform ion cyclotron resonance methods. Also, tandem mass spectrometry (MS/MS) or triple quadrupole mass spectrometry, which combines two or more mass spectrometry techniques, can be used. Conventionally known mass spectrometry using a commercially available mass spectrometry apparatus can be used as the mass spectrometry in the step P. A detection chamber or a method for processing data can also be appropriately selected.

Preferred examples of the mass spectrometry in the step P include capillary electrophoresis time-of-flight mass spectrometry (CE-TOFMS), gas chromatography-mass spectrometry (GC-MS) and liquid chromatography-mass spectrometry (LC-MS). Among them, CE-TOFMS is preferred. CE-TOFMS is excellent in the measurement of ionic low-molecular compounds, has high resolution, and can simultaneously measure more types of metabolites. CE-TOFMS is capable of measuring, for example, approximately 90% of principal metabolites of *E. coli* (Ohashi, Y., et al., "Depiction of metabolome changes in histidine-starved *Escherichia coli* by CE-TOFMS." Molecular BioSystems; 4 (2), 2008, pp. 135-147). CE-TOFMS is capable of simultaneously measuring short-chain fatty acids, amino acids, some vitamins, polyamines and the like which are principal substances as intestinal metabolites and is therefore suitable for intestinal metabolite profiling, though this method is not always suitable for the measurement of neutral substances or fat-soluble substances. GC-MS is excellent in the measurement of volatile substances such as short-chain fatty acids, but cannot measure some substances including some amino acids. LC-MS is capable of measuring diverse metabolites. However, LC-MS needs to select the optimum column and measurement method for each substance to be measured and is thus inferior in the completeness of one measurement to CE-TOFMS.

In the case of identifying the one or more substances and measuring concentration, composition or proportion of the one or more substances using mass spectrometry, substances whose types and concentrations are known can be used as internal standard substances. Examples of the internal standard substances can include methionine sulfone, D-camphor-10-sulfonic acid [CSA], 2-morpholinoethanesulfonic acid [MES], 3-aminopyrrolidine, and trimesate. The internal standard substances are preferably labeled with a stable isotope, fluorescence, or the like such that the internal standard substances can be discriminated from the substances in the fecal sample. The internal standard substances may be added to the fecal sample before the extraction of the one or more substances or may be added to a sample after the extraction of the one or more substances from the fecal sample.

The nuclear magnetic resonance spectrometry is a method which involves placing the one or more substances in a strong magnetic field, exposing molecules having uniformly oriented nuclear spins to a radiofrequency pulse for nuclear magnetic resonance, then detecting signals generated when the molecules return to their original stable states, and analyzing the molecular structures, etc.

The nuclear magnetic resonance spectrometry method is not particularly limited and may be Fourier transform NMR or may be continuous wave NMR. Also, the method may be one-dimensional NMR or may be two-dimensional NMR. The nuclear magnetic resonance spectrometry can be performed by a routine method using a commercially available nuclear magnetic resonance apparatus.

<Method for Classifying Plurality of Subjects into Two or More Clusters>

The "method for classifying a plurality of subjects into two or more clusters" of the present invention (hereinafter, also referred to as the "classification method of the present invention") is not particularly limited as long as the method comprises step Q of conducting the identification and measurement method of the present invention on each of fecal samples obtained from the plurality of subjects to identify two or more substances and to measure concentration, composition or proportion of the two or more substances; and step S of conducting cluster analysis on data of the concentration, composition or proportion of the two or more substances obtained in the step Q, and classifying the plurality of subjects into two or more clusters according to similarity of substance profiles (Subject)

The "subject" in the classification method of the present invention means an organism serving as a source of the fecal sample to be harvested. Examples of the type of this organism include, but are not particularly limited to, a mammal such as a human, a mouse, a rat, cattle, sheep, a horse, and a monkey. Among them, a human is preferred.

(Cluster)

The "cluster" for classification in the classification method of the present invention means a "population of subjects" in which the presence or absence of any one or more (preferably one) substances among the one or more substances in the fecal samples, or one or more (preferably one) characteristics selected from high and low concentrations, etc. are common.

(Step Q)

The step Q in the classification method of the present invention is not particularly limited as long as the step is of conducting the identification and measurement method of the present invention on each of fecal samples obtained from the plurality of subjects to identify two or more substances and to measure concentration, composition or proportion of the two or more substances.

(Step S)

The step S in the classification method of the present invention is not particularly limited as long as the step is of conducting cluster analysis on data of the concentration, composition or proportion of the two or more substances obtained in the step Q, and classifying the plurality of subjects into two or more clusters according to similarity of substance profiles. The approach for the cluster analysis in the step S is not particularly limited as long as the plurality of subjects can be classified into two or more clusters. The approach may be hierarchical clustering or may be partitional optimization clustering. Examples of the partitional optimization clustering can preferably include PAM clustering (partitioning around medoid clustering). The cluster analysis can be conducted using commercially available software.

The "similarity of substance profiles" in the step S means the degree to which the types of the two or more substances identified in the step Q, or the concentration, composition or proportion of the two or more substances measured in the step Q are similar between a certain subject and another subject. The similarity can be evaluated using commercially available cluster analysis software or the like.

Examples of the number of clusters for classification can preferably include, but are not particularly limited to, the number of clusters drawn on the basis of Calinski-Harabasz (CH) index. However, if clustering at the number of clusters drawn on the basis of the CH index causes an error, the substances can be preferably classified into the number of clusters larger by one than the number of clusters drawn.

(Step R)

The classification method of the present invention does not have to further comprise step R between the step Q and the step S and may further comprise step R. The step R is not particularly limited as long as the step is of standardizing the data of the concentration, composition or proportion of the two or more substances obtained in the step Q. This standardization of the data can be performed using commercially available software or the like.

Hereinafter, the present invention will be described in detail with reference to Examples. However, the present invention is not limited by these Examples.

Example 1

1. Extraction of Metabolite—1

In order to detect metabolites of intestinal microbiota in a fecal sample using a capillary electrophoresis (CE) time-of-flight mass spectrometer (TOFMS) (CE-TOFMS), first, study was conducted on a condition for extracting the metabolites.

1-1 Method 1-1-1 Method for Extracting Metabolite

[1] A fecal sample was harvested from a healthy human and preserved at −80° C. immediately after the harvesting.

[2] A 0.1×PBS solution (hereinafter, simply referred to as a "PBS solution") containing 3 internal standard substances (20 μM methionine sulfone, 20 μM D-camphor-10-sulfonic acid [CSA] and 20 μM 2-morpholinoethanesulfonic acid [MES]) was added at a ratio of 100 μL per 10 mg of the fecal sample and stirred using a handy homogenizer (manufactured by Sigma-Aldrich Co. LLC) until the whole fecal sample became uniform, to prepare a fecal suspension.

[3] 100 μL of the fecal suspension was dispensed to each of four screw capped tubes (manufactured by Bio-Medical Science Co., Ltd.), and extraction samples 1 and 2 to 5 were respectively obtained under extraction conditions shown in the following [4] to [9] (FIG. 1 and Table 1).

[4] 100 μL of the fecal suspension prepared in the step [3] was centrifuged at 17,800×g for 10 minutes to recover a supernatant (supernatant a). To the precipitate after removal of the supernatant a, a PBS solution was added at a ratio of 100 μL per 10 mg of the fecal sample, and stirred in a vortex mixer, followed by the recovery of a supernatant (supernatant b). Proteins were removed from each of the supernatant a and the supernatant b through an ultrafiltration filter having a molecular weight cutoff of 5 kDa. The filtrates were diluted two-fold with Milli-Q water and used in measurement. Concentrations obtained from the supernatant a and the supernatant b after the measurement were added up, and the resultant was used as extraction sample 1.

[5] To the precipitate after the removal of the supernatant b in the step [4], 100 μL of a PBS solution was added per 10 mg of the fecal sample, stirred in a vortex mixer, and then centrifuged at 17,800×g for 10 minutes. Then, a washing step of removing the supernatant was repeated twice to remove extracellular metabolites and the internal standard substances. To the precipitate, 100 μL of a 50% methanol solution/Milli-Q water containing the 3 internal standard substances, three 3 mm zirconia beads (manufactured by Tomy Seiko Co., Ltd.), and approximately 0.1 g of 0.1 mm zirconia beads (manufactured by Tomy Seiko Co., Ltd.) were added, and stirred at 1,500 rpm for 10 minutes using Shake Master NEO (manufactured by Bio-Medical Science Co., Ltd.) to perform cell disruption treatment. Then, a supernatant ("extraction sample 2") was recovered by centrifugation at 17,800×g for 5 minutes. Proteins were removed from the extraction sample through an ultrafiltration filter having a molecular weight cutoff of 5 kDa. The filtrate was dried at 40° C. for 3 hours in a vacuum dryer (manufactured by Labconco Corp.) and then redissolved in 50 μL of Milli-Q water, and the resultant was used in measurement.

[6] 100 μL of the fecal suspension prepared in the step [3] was stirred at 1,500 rpm for 10 minutes using Shake Master NEO (manufactured by Bio-Medical Science Co., Ltd.). In this operation, no beads were added. Then, a supernatant ("extraction sample 3") was recovered by centrifugation at 17,800×g for 5 minutes. Proteins were removed from the extraction sample 3 through an ultrafiltration filter having a molecular weight cutoff of kDa. The filtrate was diluted two-fold with Milli-Q water, and the resultant was used in measurement.

[7] To 100 μL of the fecal suspension prepared in the step [3], three 3 mm zirconia beads (manufactured by Tomy Seiko Co., Ltd.) and approximately 0.1 g of 0.1 mm zirconia beads (manufactured by Tomy Seiko Co., Ltd.) were added, and stirred at 1,500 rpm for 10 minutes using Shake Master NEO (manufactured by Bio-Medical Science Co., Ltd.) to perform cell disruption treatment. Then, a supernatant ("extraction sample 4") was recovered by centrifugation at 17,800×g for 5 minutes. Proteins were removed from the extraction sample 4 through an ultrafiltration filter having a molecular weight cutoff of 5 kDa. The filtrate was dried at 40° C. for 3 hours in a vacuum dryer (manufactured by Labconco Corp.) and then redissolved in 50 μL of Milli-Q water, and the resultant was used in measurement.

[8] To 100 μL of the fecal suspension prepared in the step [3], 100 μL of a 100% methanol solution (final concentration: 50% methanol), three 3 mm zirconia beads (manufactured by Tomy Seiko Co., Ltd.), and approximately 0.1 g of 0.1 mm zirconia beads (manufactured by Tomy Seiko Co., Ltd.) were added, and stirred at 1,500 rpm for 10 minutes using Shake Master NEO (manufactured by Bio-Medical Science Co., Ltd.) to perform cell disruption treatment. Then, a supernatant ("extraction sample 5") was recovered by centrifugation at 17,800×g for 5 minutes. Proteins were removed from the extraction sample through an ultrafiltration filter having a molecular weight cutoff of 5 kDa. The filtrate was dried at 40° C. for 3 hours in a vacuum dryer (manufactured by Labconco Corp.) and then redissolved in 50 μL of Milli-Q water, and the resultant was used in measurement.

TABLE 1

| Extraction sample (extraction condition) | Fraction | Extraction solvent | Presence or absence of disruption treatment |
| --- | --- | --- | --- |
| 1 | Supernatant of fecal suspension (extraction twice) | 0.1 × PBS | x |
| 2 | Precipitate of fecal suspension | 50% methanol/ water | o |
| 3 | Fecal suspension | 0.1 × PBS | x |
| 4 | Fecal suspension | 0.1 × PBS | o |
| 5 | Fecal suspension | 50% methanol/ 0.1 × PBS | o |

1-1-2 Measurement and Analysis of Metabolite by CE-TOFMS

The extraction samples were measured on the cation mode of CE-TOFMS (manufactured by Agilent Technologies, Inc.). The measurement by CE-TOFMS was performed according to the method described in the document (Hirayama, A., et al., "Quantitative metabolome profiling of colon and stomach cancer microenvironment by capillary electrophoresis time-of-flight mass spectrometry." Cancer Research; 69 (11) 2009, pp. 4918-4925). On the basis of the measurement data of CE-TOFMS, the identification of the metabolites and the calculation of their concentrations were performed using analytical software Master Hands (Sugimoto, M., et al., "Capillary electrophoresis mass spectrometry-based saliva metabolomics identified oral, breast and pancreatic cancer-specific profiles." Metabolomics: Official journal of the Metabolomic Society; 6 (1), 2010, pp. 78-95). In order to compare the metabolite concentrations among the extraction conditions, z-scores were calculated from the metabolite concentrations of each condition (i.e., the metabolite concentrations of each condition were standardized), and heat maps were prepared using MeV TM4 version 4.8 (Saeed, A. I., et al., "TM4 microarray software suite." Methods in Enzymology 2006; 411: 134-193), followed by the clustering of the metabolites using k-means. The types and concentrations of the identified metabolites hierarchically clustered among the extraction samples.

1-2 Results and Discussion

In order to compare the metabolite concentrations among the extraction conditions, the concentration of each metabolite was converted to a z-score to visualize the types and concentrations of the obtained metabolites. The metabolites were classified by k-means clustering into clusters I to IV reflecting the features of each extraction condition (FIG. 2).

45 types of metabolites were classified into the cluster I (Table 2).

TABLE 2

| Cluster I | | |
| --- | --- | --- |
| Gly | Gln | Tyr |
| Thymine | Urocanate | Val |
| Glu-Glu | Xanthine | Carnosine |

TABLE 2-continued

Cluster I

| | | |
|---|---|---|
| Ectoine | Hydroxyproline | Alpha-Methylserine |
| Trimethylamine N-oxide | Ala | Asn |
| N-Acetylglucosamine | 2AB (DL-α-Amino-n-butyric acid) | Citrulline |
| Cytosine | Gly-Gly | Gly-Leu |
| Ile | Leu | Lys |
| Met | Ornithine | Phe |
| Pro | Ser | Trp |
| Thr | Uracil | Putrescine(1,4-Butanediamine) |
| Thymidine | Cystine | N6,N6,N6-Trimethyllysine |
| Homoserine | Mannosamine | Glycerophosphorylcholine |
| 5-Methyltetrahydrofolate | Synephrine | Isoamylamine |
| Carbachol | Pterin | Guanidinosuccinate |

The metabolite group of this cluster I was detected at the highest concentration in the extraction sample 4 (involving disruption treatment with beads). This cluster I included 15 amino acids and 3 dipeptides. Also, the metabolites of this cluster I tended to be detected at a higher concentration in the extraction sample 4 (involving disruption treatment with beads) than in the extraction sample 3 (without disruption treatment with beads) (FIG. 3). Therefore, it is considered that these metabolites not only exist outside bacterial cells but exist in given amounts within the bacterial cells and were thus detected in increased amounts by bacterial cell disruption with beads. Furthermore, these metabolites of the cluster I tended to be detected at a higher concentration in the extraction sample 4 (extraction with PBS) than in the extraction sample 5 (extraction with methanol) and were therefore found difficult to elute into methanol (FIG. 3).

23 types of metabolites were classified into the cluster II (Table 3).

TABLE 3

Cluster II

| | | |
|---|---|---|
| Arg | alpha-Aminoadipate | Methionine sulfoxide |
| N8-Acetylspermidine | Cytidine | beta-Ala-Lys |
| Taurine | 5-Methyl-2'-deoxycytidine | Thiamine |
| alpha-Lipoamide | Pyridoxal | N-Acetylhistidine |
| Ala-Ala | 2'-Deoxycytidine | Guanine |
| 2'-Deoxyguanosine | 5-Hydroxyindoleacetate | Adenosine |
| 5'-Deoxyadenosine | N6-Methyl-2'-deoxyadenosine | Riboflavin |
| N-alpha,N-alpha-Dimethylhistidine | trans-Zeatin | |

The metabolite group of this cluster II was detected at a high concentration, particularly, in the extraction sample 5. These metabolites tended to be extracted at the highest concentration under the condition involving disruption with Beads and addition of methanol. Therefore, the metabolites are considered to be highly abundant within bacterial cells and be easily soluble in methanol. This cluster included nucleic acid constituents such as guanine, cytidine and adenosine, and vitamins such as thiamine and pyridoxal.

52 types of metabolites were classified into the cluster III (Table 4).

TABLE 4

Cluster III

| | | |
|---|---|---|
| Cadaverine | gamma-Butyrobetaine | Dihydrouracil |
| Uridine | 5-Aminovalerate | 7-Methylguanine |
| Pyridoxamine | N,N-Dimethylglycine | N-Methylalanine |
| 6-Aminohexanoate | N-Acetylglucosylamine | Indole-3-acetate |
| 2-Deoxystreptamine | Muramate | GABA |
| Asp | beta-Ala | Choline |
| Glu | His | Hypoxanthine |
| Piperidine | Pipecolate | 5-Oxoproline |
| Allantoin | N-Acetylputrescine | Carnitine |
| Octopine | Spermidine | Sarcosine |
| 5-Hydroxylysine | Inosine | 3-Methylguanine |
| 5-Methoxyindoleacetate | Tyramine | Tyrosine methyl ester |
| N-epsilon-Acetyllysine | Glucosamine | Isopropanolamine |
| N-Methylglutamate | Creatine | N-gamma-Ethylglutamine |
| Pyridoxamine 5'-phosphate | Creatinine | p-Aminobenzoate |
| Castanospermine | N-Acetylornithine | Guanosine |
| Histamine | 3-Methylhistidine | Indole-3-acetamide |
| Eflornithine | | |

The metabolite group of this cluster III was detected in small amounts in the extraction sample 2 and detected at the same level among the extraction samples 1 and 3 to 5. Also because the amounts of the metabolites detected were less different between the extraction sample (without disruption treatment with beads) and the extraction sample 4 (involving disruption treatment with beads), these metabolites were found low abundant within bacterial cells. The extraction sample 4 (extraction with PBS) and the extraction sample 5 (extraction with methanol), when compared, did not largely differ in detected concentrations. Therefore, the metabolites were found extractable with PBS or with methanol at the same level.

21 types of metabolites (Table 5) were classified into the cluster IV.

TABLE 5

Cluster IV

| | | |
|---|---|---|
| Leu-Leu-Tyr | Pyridoxine | Urea |
| 2,4-Diaminobutyrate | 3-Methyladenine | Purine riboside |
| N-Acetylvaline | Ethanolamine phosphate | gamma-Glu-2AB |
| Diethanolamine | 5-Aminoimidazole-4-carboxamide ribotide | Anserine |
| o-Acetylcarnitine | Adenine | 3-Aminopropane-1,2-diol |
| Epinephrine | Purine | Sepiapterin |
| Tetrahydropalmatine | Cyclohexylamine | Phenylethanolamine |

The metabolite group of this cluster IV was not detected under several extraction conditions. Thus, it is considered that an extraction condition needs to be carefully studied in focusing on these metabolites.

When the features of each extraction condition were compared by hierarchical clustering among the samples in light of the results described above, almost all the metabolite concentrations in the extraction sample 2 were found low as compared with the other extraction methods. This indicates that most of metabolites in feces exist outside bacterial cells. Since the growth or lysis (death) of intestinal microbiota occurs constantly in the intestinal tracts, metabolites derived from lysed intestinal microbiota are considered to also exist in large amounts in the intestinal tracts or in feces. In the extraction sample 2, metabolites contained in bacterial cells that existed in feces without being lysed were detected. The metabolite concentrations detected in the extraction sample 2 were low concentrations as a whole, suggesting that the amounts of metabolites contained in such cells are very small with respect to the whole. As for the other extraction conditions, the results of hierarchical clustering showed that the extraction sample and the extraction sample 3 were similar. The extraction approaches of the extraction sample 1 and the extraction sample 3 differed only in that stirring was performed for the extraction sample 3, whereas no stirring was performed for the extraction sample 1. The other conditions such as an extraction solvent were the same between these extraction samples. Since beads were not used in the stirring for the extraction sample 3, it appears that bacterial cell disruption did not occur. The results of this study indicate that metabolites in feces exist mainly outside bacterial cells, suggesting that the extraction sample 1 and the extraction sample 3 eventually established similar extraction conditions. An approach that produced similar metabolite profiles following the extraction sample 1 and the extraction sample 3 was the extraction sample 4. The extraction sample 3 and the extraction sample 4 were similar in metabolite profiles, except for amino acids, etc. belonging to the cluster I, in spite of difference in the presence or absence of disruption with beads. The extraction sample 5 was classified into a cluster different from that of the extraction sample 1, the extraction sample 3, and the extraction sample 4. The extraction sample 1, the extraction sample 3, and the extraction sample 4 involved no methanol in the solvent, whereas the extraction sample involved methanol in the solvent, indicating that difference in solvent influences the resulting metabolite profile. The extraction sample 3 and the extraction sample 4 differed in the presence or absence of disruption with beads, and the extraction sample 4 and the extraction sample 5 differed in the presence or absence of methanol addition. The difference between the extraction sample 4 and the extraction sample 5 was found larger than that between the extraction sample 3 and the extraction sample 4, indicating that the presence or absence of methanol addition has greater influence than that of the presence or absence of disruption with beads.

Subsequently, individual metabolites were focused on to examine metabolites that differed significantly in concentration depending on difference in solvent or the presence or absence of bacterial cell disruption. The extraction sample 4 and the extraction sample 5 were compared in analysis on the influence of the difference in solvent, and the extraction sample 3 and the extraction sample 4 were compared in analysis on the influence of the presence or absence of bacterial cell disruption. As a result of the comparison, substances having significant difference with a false discovery rate (FDR) of 0.05 or less were selected.

Among 141 substances detected from the comparison for the difference in solvent (comparison between the extraction sample 4 and the extraction sample 5), the metabolite concentrations of 29 substances exhibited significant difference based on the difference in solvent (Table 6). Among them, 14 substances were amino acids and were all detected at a significantly high concentration in the extraction sample 4. Such results were obtained probably because amino acids become zwitterions in an aqueous solution and have the property of being more soluble in water than in an organic solvent. Substances having a significantly high concentration in the extraction sample 5 supplemented with methanol included nucleic acid constituents such as adenine and 2'-deoxyguanosine.

TABLE 6

Type of solvent that permitted detection at high concentration

| | Metabolite name | FDR |
|---|---|---|
| 0.1 × PBS (condition 4) | Met | 0.009 |
| | Ile | 0.009 |
| | Val | 0.009 |
| | Thr | 0.009 |
| | N-Acetylglucosamine | 0.014 |
| | Gly-Leu | 0.015 |
| | Urocanate | 0.015 |
| | Pro | 0.016 |
| | Putrescine(1,4-Butanediamine) | 0.017 |
| | Ala | 0.019 |
| | Gly | 0.019 |
| | Lys | 0.021 |
| | Gln | 0.024 |
| | Trp | 0.024 |
| | Phe | 0.024 |
| | Uracil | 0.024 |
| | Tyr | 0.024 |
| | Dihydrouracil | 0.025 |
| | Glu | 0.026 |
| | Asp | 0.035 |
| | Cadaverine | 0.036 |
| | Thymine | 0.037 |
| | Hypoxanthine | 0.038 |
| | Gly-Gly | 0.042 |
| | Ornithine | 0.042 |
| 50% methanol/0.1 PBS (condition 5) | Adenine | 0.021 |
| | Pipecolate | 0.037 |
| | 2'-Deoxyguanosine | 0.042 |
| | 3-Aminopropane-1,2-diol | 0.044 |

From the comparison for the presence or absence of bacterial cell disruption with beads (comparison between the extraction sample 3 and the extraction sample 4), the metabolite concentrations of 7 substances including 4 amino acids exhibited significant difference (Table 7). All these metabolites had a high concentration in the extraction sample 4 subjected to bacterial cell disruption.

TABLE 7

Condition that permitted detection at high concentration

| | Metabolite name | FDR |
|---|---|---|
| Bacterial cell disruption with beads (condition 4) | Met | 0.037 |
| | Asn | 0.037 |
| | Val | 0.037 |
| | Phe | 0.037 |
| | Choline | 0.037 |
| | Citrulline | 0.037 |
| | Gly-Leu | 0.050 |

As a result of analyzing the numbers of metabolites that were able to be detected in the extraction samples 1 to 5, the number of metabolites detected in the extraction sample 5 was 131 on average and was thus largest (FIG. 4). This is probably because: unlike the extraction sample 1 and the extraction sample 2, bacterial cells were not separated from a supernatant; and use of an organic solvent also permitted extraction of metabolites poorly soluble in a PBS solution. The number of metabolites detected in the extraction sample 2 was 83 on average and was thus smallest. This study indicates that the abundance of metabolites within bacterial cells is smaller than that outside bacterial cells. This result indicates that approximately 30 to 40% substances that fall short of the detection limit are present even if metabolites are obtained only from within bacterial cells.

These results showed that cationic metabolite profiles in feces obtained by CE-TOFMS are influenced by a Solvent used in extraction or the presence or absence of bacterial cell disruption with beads. The comparison of metabolite profiles among the supernatant fraction, the precipitate fraction, and the whole fecal suspension demonstrated that diverse metabolites are contained in the supernatant fraction. In the comparison among the extraction samples 1 to 5, particularly, amino acid concentrations tended to be susceptible to an extraction condition and be detected with the highest concentration in the extraction sample 4 subjected to bacterial cell disruption without being supplemented with methanol. In the comparison of the numbers of detectable metabolites, the most types of metabolites were detected in the extraction sample 5 supplemented with methanol and subjected to bacterial cell disruption with beads.

Example 2

2. Extraction of Metabolite—2

The metabolite extraction condition was further studied on the basis of the condition that offered the extraction sample 5. Specifically, difference in detectable metabolites between metabolite extraction using methanol as a solvent (hereinafter, referred to as a "methanol method"), as in the condition that offered the extraction sample 5, and metabolite extraction using methanol and chloroform as a solvent (hereinafter, referred to as a "methanol-chloroform method") was analyzed by CE-TOFMS.

2-1 Method 2-1-1 Methanol Method

[1] A fecal sample was harvested from each of healthy humans (75 male and female persons in total) and subjected to freeze drying treatment.

[2] To the fecal sample thus freeze-dried, four 3 mm zirconia beads (manufactured by Tomy Seiko Co., Ltd.) were added, and stirred using Shake Master NEO (manufactured by Bio-Medical Science Co., Ltd.) until the whole fecal sample became uniform.

[3] To 10 mg of the fecal sample thus stirred, 400 μL of 50% methanol containing the 3 internal standard substances (20 μM methionine sulfone, 20 μM D-camphor-10-sulfonic acid [CSA] and 20 μM 2-morpholinoethanesulfonic acid [MES]) and 0.1 g of 0.1 mm zirconia beads (manufactured by Tomy Seiko Co., Ltd.) were added, and stirred at 1,500 rpm for 10 minutes using Shake Master NEO (manufactured by Bio-Medical Science Co., Ltd.) to perform cell disruption treatment. Then, a supernatant ("extraction sample Me") was recovered by centrifugation at 15,000 rpm at 4° C. for 5 minutes. Proteins were removed from the extraction sample Me through an ultrafiltration filter having a molecular weight cutoff of 5 kDa. The filtrate was dried at 40° C. for 3 hours in a vacuum dryer (manufactured by Labconco Corp.). Then, 100 μL of Milli-Q water containing 2 internal standard substances (200 μM 3-aminopyrrolidine and 200 μM trimesate) was added thereto and well stirred for redissolution, and the resultant was used in measurement.

2-1-2 Methanol-Chloroform Method

To 10 mg of the fecal sample stirred in the step [2] of the section "2-1-1 Methanol method", 500 μl of 100% methanol containing the 3 internal standard substances (20 μM methionine sulfone, 20 μM D-camphor-10-sulfonic acid [CSA] and 20 μM 2-morpholinoethanesulfonic acid [MES]) and 0.1 g of 0.1 mm zirconia beads (manufactured by Tomy Seiko Co., Ltd.) were added, further 500 μL of chloroform and 200 μL of Milli-Q water were added, and then stirred at 1,500 rpm for 10 minutes using Shake Master NEO (manufactured by Bio-Medical Science Co., Ltd.) to perform cell disruption treatment. Then, a supernatant ("extraction sample MeCr") was recovered by centrifugation at 15,000 rpm at 4° C. for 5 minutes. Proteins were removed from the extraction sample MeCr through an ultrafiltration filter having a molecular weight cutoff of 5 kDa. The filtrate was dried at 40° C. for 3 hours in a vacuum dryer (manufactured by Labconco Corp.). Then, 100 μL of Milli-Q water containing 2 internal standard substances (200 μM 3-aminopyrrolidine and 200 μM trimesate) was added thereto and well stirred for redissolution, and the resultant was used in measurement.

2-1-3 Measurement and Analysis of Metabolite by CE-TOFMS

The measurement and analysis of metabolites by CE-TOFMS were conducted by the method described in the section "1-1-2 Measurement and analysis of metabolite by CE-TOFMS", and in addition, measurement was also conducted on the anion mode to calculate metabolite concentrations.

2-2 Results

The profiles of metabolites extracted by the methanol method were very similar to the profiles of metabolites extracted by the methanol-chloroform method. On the other hand, as a result of comparing the concentrations of the metabolites extracted by these two types of extraction methods, the detected metabolite concentrations were higher as a whole in the extraction by the methanol method than by the methanol-chloroform method. Specifically, metabolites that exhibited 1.5-fold or more difference between the methods were 29 types of substances shown in Table 8. Among them, 4 types of metabolites had a higher detected concentration in the extraction by the methanol-chloroform method, whereas metabolites as many as 25 types exhibited a higher detected concentration in the extraction by the methanol method (Table 8).

TABLE 8

| Metabolite | Me | MeCr | MeCr/Me |
| --- | --- | --- | --- |
| Trimethylamine N-oxide | 0.199 | 0.003 | 0.016 |
| Sarcosine | 4.002 | 0.090 | 0.022 |
| Adenosine | 0.276 | 0.034 | 0.122 |
| Adenine | 0.152 | 0.026 | 0.172 |
| Pyridoxamine | 0.045 | 0.018 | 0.399 |
| Gly-Leu | 0.259 | 0.108 | 0.418 |
| Thr | 0.590 | 0.273 | 0.462 |
| Guanosine | 0.064 | 0.032 | 0.499 |
| alpha-Aminoadipate | 0.142 | 0.072 | 0.506 |
| Thymidine | 0.550 | 0.296 | 0.538 |
| Met | 0.570 | 0.316 | 0.554 |
| N8-Acetylspermidine | 0.248 | 0.138 | 0.557 |
| Tyramine | 0.183 | 0.104 | 0.569 |
| Leu | 2.001 | 1.162 | 0.580 |
| Phenylethanolamine | 0.277 | 0.162 | 0.583 |
| Isopropanolamine | 0.325 | 0.194 | 0.596 |
| Arg | 1.521 | 0.943 | 0.620 |
| Ile | 2.002 | 1.271 | 0.635 |
| Propionate | 82.999 | 55.560 | 0.669 |
| Asp | 6.182 | 4.403 | 0.712 |
| N1-Acetylspermidine | 0.290 | 0.208 | 0.717 |
| Ser | 0.630 | 0.459 | 0.729 |
| Phe | 1.929 | 1.425 | 0.739 |
| Gly | 4.525 | 3.346 | 0.740 |
| Choline | 0.286 | 0.213 | 0.746 |
| Glutarate | 1.340 | 2.026 | 1.512 |
| Lactate | 1.920 | 3.137 | 1.634 |
| Diethanolamine | 0.047 | 0.078 | 1.640 |
| Alpha-Methylserine | 0.383 | 0.646 | 1.689 |

The numerical values in the second and third columns from the left in Table 8 represent the concentrations (relative value to the internal standard substances) of each metabolite detected in "Me (extraction sample Me)" and "MeCr (extraction sample MeCr)", respectively. The numerical values in the first column from the right in the table represent the ratio of the concentration of each metabolite detected in "MeCr (extraction sample MeCr)" to the concentration of each metabolite detected in "Me (extraction sample Me)", MeCr/Me.

The organizations of human intestinal microbiota are considered to be divided into two or three enterotypes according to the features of diets. Accordingly, a fecal Sample was harvested 9 times per test subject from 18 healthy test subjects. All metabolites detected according to the method described in the section "2-1-1 Methanol method" were used and classified by PAM clustering into the enterotypes according to the method described in the document (Arumugam, M., et al., "Enterotypes of the human gut microbiome." Nature; 473 (7346), 2011, pp. 174-180). As a result of conducting PAM clustering by setting the number of clusters suitable for classification to 3, the metabolites were able to be classified into butyrate, cholate, and thiamine groups (FIG. 5).

Example 3

3. Extraction of Metabolite—3
3-1-1 Extraction with PBS Solution
[1] A fecal sample was harvested from a healthy human and subjected to freeze drying treatment.
[2] To 10 mg of the fecal sample thus freeze-dried, 500 μL of a 1×PBS solution containing the 3 internal standard substances (20 μM methionine sulfone, 20 μM D-camphor-10-sulfonic acid [CSA] and 20 μM 2-morpholinoethanesulfonic acid [MES]), four 3 mm zirconia beads (manufactured by Tomy Seiko Co., Ltd.), and approximately 0.1 g of 0.1 mm zirconia beads (manufactured by Tomy Seiko Co., Ltd.) were added, and stirred at 1,500 rpm for 5 minutes using Shake Master NEO (manufactured by Bio-Medical Science Co., Ltd.) to perform cell disruption treatment. Then, a supernatant ("extraction sample PBS solution") was recovered by centrifugation at 15,000 rpm at 4° C. for 5 minutes. Proteins were removed from the extraction sample PBS solution through an ultrafiltration filter having a molecular weight cutoff of 5 kDa. The filtrate was dried at 40° C. for 3 hours in a vacuum dryer (manufactured by Labconco Corp.). Then, 20 μL of Milli-Q water containing 2 internal standard substances (200 μM 3-aminopyrrolidine and 200 μM trimesate) was added thereto and well stirred for redissolution. The enrichment factor of this solution from the initial suspension of the fecal sample (hereinafter, also referred to as the "enrichment factor of this solution") was 15-fold, and the PBS concentration of this solution was 15×PBS. This solution was diluted by the addition of Milli-Q water such that the enrichment factor of this solution from the initial suspension of the fecal sample was 10-fold (×10), 5-fold (×5), 1-fold (×1), or 0.2-fold (×0.2). These dilutions were analyzed by CE-TOFMS.
3-1-2 Extraction with Water
The same extraction treatment as in the section "3-1-1 Extraction with PBS solution" was performed except that Milli-Q water containing the 3 internal standard substances (20 μM methionine sulfone, 20 μM D-camphor-10-sulfonic acid [CSA] and 20 μM 2-morpholinoethanesulfonic acid [MES]) was used instead of the "1×PBS solution containing the 3 internal standard substances (20 μM methionine sulfone, 20 μM D-camphor-10-sulfonic acid [CSA] and 20 μM 2-morpholinoethanesulfonic acid [MES])" in the step [2]. Each dilution obtained was analyzed by CE-TOFMS.
3-1-3 Measurement and Analysis of Metabolite by CE-TOFMS The measurement and analysis of metabolites in each dilution obtained in the section 3-1-1 or 3-1-2, by CE-TOFMS were conducted by the method described in the section "1-1-2 Measurement and analysis of metabolite by CE-TOFMS", and in addition, measurement was also conducted on the anion mode to calculate metabolite concentrations.
3-2 Results The number of types of metabolites detected in each dilution is shown in FIG. 6. In the case of the extraction with a PBS solution, current flowed excessively in the samples with an enrichment factor of 5-fold or more (×5, ×10, and ×15 in PBS) due to the influence of a salt concentration so that accurate measurement was unable to be performed. As a result of comparing the number of types of detected metabolites between the ×0.2 or ×1 dilution (sample) of the extract with a PBS solution and the ×0.2 or ×1 dilution (sample) of the extract with water, metabolites were detected at a proportion larger by approximately 11 to 17% in the water extraction sample than in the PBS extraction sample (FIG. 6).

The extraction with water presented no problem in current value even at an enrichment factor of 5-fold or more, but tended to have a slightly broad shape of a peak, particularly, in the measurement on the anion mode. Thus, it was found desirable to conduct measurement at an enrichment factor of 1-fold or less, for the measurement on the anion mode of the extract with water.

Example 4

4. Study on Method for Preserving Fecal Sample—1
Study was conducted on how the state of preservation of a fecal sample after the harvesting of the fecal sample and before the detection of metabolites would influence the detection of metabolites. Specifically, a fecal sample was harvested from a healthy human and preserved at room temperature (20 to 25° C.) for 1 to 2 days. Then, metabolites were extracted with 50% methanol as a solvent according to the method described in Example 2, and measured by CE-TOFMS. The measurement was conducted on the anion mode in addition to the method described in Example 1. A fecal sample was harvested from a healthy human and immediately preserved in an ultralow-temperature freezer (−80° C.), and the resultant was used as a control.

As a result, the preservation of the fecal sample at room temperature for 1 to 2 days after harvesting was confirmed to increase or decrease the concentrations of at least 47 types of metabolites as compared with the preservation at −80° C. (FIG. 7). For example, in FIG. 7, "I" depicts metabolites that exhibited increase in concentration by the preservation of the fecal sample at room temperature for 1 to 2 days. "II" depicts metabolites that exhibited increase in concentration by the preservation of the fecal sample at room temperature for 1 day and decrease in concentration by the preservation at room temperature for 2 days. "III" depicts metabolites that exhibited decrease in concentration by the preservation of the fecal sample at room temperature for 1 to 2 days. For example, 10 types of metabolites such as butanoate (butyrate) and propionate had 2-fold or more increase in their concentrations, whereas the concentrations of 10 types of metabolites such as cholate were decreased to ½ or lower (FIG. 7). The preservation period of 2 days rather than 1 day had a higher rate of increase or decrease in metabolite concentrations as compared with the preservation at −80° C.

Further study was also conducted on the preservation of a harvested fecal sample under refrigeration (4° C.) or freezing (−20° C.) and the extraction of metabolites by the "methanol-chloroform method". As a result, the preservation of the fecal sample at 4° C. and the extraction of metabolites by the "methanol-chloroform method" were similarly confirmed to increase or decrease metabolite concentrations as compared with the preservation at −80° C., while the preservation period of 2 days rather than 1 day had a higher rate of increase or decrease in metabolite concentrations (FIGS. 8 and 9). On the other hand, the preservation of the fecal sample at −20° C. exhibited metabolite profiles similar to those of the preservation at −80° C. (FIG. 10).

These results indicate that the preservation of a fecal sample under freezing (at least −20° C. or lower) can favorably maintain metabolite profiles in the fecal sample immediately after harvesting, whereas the preservation of a fecal sample under refrigeration or at ordinary temperature hardly maintains metabolite profiles in the fecal sample immediately after harvesting due to variations in metabolite profiles. Particularly, when a fecal sample was preserved under refrigeration or at ordinary temperature, the concentrations of metabolites such as 4-beta-acetylaminoethyl imidazole, riboflavin, octanoate, beta-Ala, quinate, malate, and choline were shown to differ in the manner of increase and decrease among individual test subjects in such a way that the concentrations were increased in a fecal sample obtained from a certain test subject whereas the concentrations were decreased in a fecal sample obtained from another test subject. This result suggests the possibility that when fecal samples are preserved under refrigeration or at ordinary temperature, the manner of change in metabolite profiles differs depending on different microbiota or different metabolites contained in the fecal samples even preserved in the same way. Therefore, it is difficult to predict metabolite profiles in a fecal sample immediately after harvesting from metabolite profiles in the fecal sample after preservation, on the basis of variations in metabolite profiles caused by the preservation of the fecal sample under refrigeration or at ordinary temperature. Hence, it is considered that variations in metabolite profiles caused by the preservation of the fecal sample need to be minimized.

Example 5

5. Study on method for preserving fecal sample—2

In some situations, a fecal sample may be difficult to preserve under freezing immediately after harvesting, for example, when the fecal sample is harvested at a site without freezing equipment and delivered to a distant analysis facility. Accordingly, in order to study a preservation method other than freezing, analysis was conducted on how metabolite profiles would vary when a fecal sample was preserved in various organic solvents (100% methanol [100% MeOH], 50% methanol [50% MeOH], or methanol-chloroform [MeOH/CHCl$_3$]). Specifically, study was conducted on a method of preserving a fecal sample in a 100% methanol solution and then extracting metabolites with a methanol-chloroform solution ("Method 1" of Table 9), a method of preserving a fecal sample in a 50% methanol solution and then extracting metabolites with a methanol-chloroform solution ("Method 2" of Table 9), a method of preserving a fecal sample in a 50% methanol solution and then extracting metabolites with methanol and PCI (phenol-chloroform-isoamyl alcohol; 25:24:1) solutions ("Method 3" of Table 9), and a method of preserving a fecal sample in a methanol-chloroform solution and then extracting metabolites with a methanol-chloroform solution ("Method 4" of Table 9). A method of preserving a fecal sample in the absence of the organic solvent and then extracting metabolites with a methanol-chloroform solution ("Method C" of Table 9) was performed as a control. In each extraction method, a fecal sample was preserved at −80° C. immediately after addition into each organic solvent (methods 1 to 4), or a fecal sample was immediately preserved at −80° C. in the absence of the organic solvent (method C), and the resulting sample was used as a control. The detailed method will be given below.

5-1 Method

[1] A fecal sample was harvested from a healthy human, and its weight was measured. A solvent for preservation ("Solvent for preservation" of Table 9) was added thereto.

[2] The fecal sample was preserved at room temperature (20 to 25° C.), 4° C., or −80° C. for 2 days.

[3] The solvent for preservation was added to a solvent for addition ("Solvent for addition" of Table 9) so as to attain each metabolite extraction condition ("Composition of extraction solvent" of Table 9). In this operation, 10 µL of Milli-Q water containing 3 internal standard substances (1000 µM methionine sulfone, 1000 µM D-camphor-10-sulfonic acid [CSA] and 1000 µM 2-morpholinoethanesulfonic acid [MES]) was added.

[4] Three 3 mm zirconia beads (manufactured by Tomy Seiko Co., Ltd.) and approximately 0.1 g of 0.1 mm zirconia beads (manufactured by Tomy Seiko Co., Ltd.) were added thereto, and stirred at 1,500 rpm for 10 minutes using Shake Master NEO (manufactured by Bio-Medical Science Co., Ltd.) to perform cell disruption treatment.

[5] A supernatant was recovered by centrifugation at 15,000 rpm at 4° C. for 5 minutes. Then, proteins were removed from the supernatant through an ultrafiltration filter having a molecular weight cutoff of 5 kDa. The filtrate was dried at 40° C. for 3 hours in a vacuum dryer (manufactured by Labconco Corp.) and then redissolved in 100 µL of Milli-Q water containing 2 internal standard substances (200 µM 3-aminopyrrolidine and 200 µM trimesate). Metabolites were measured by CE-TOFMS according to the method described in Example 1.

TABLE 9

| Method | Solvent for preservation (µL) | | | Solvent for addition (µL) | | | | Composition of extraction solvent (µL) | | | |
|---|---|---|---|---|---|---|---|---|---|---|---|
| | CHCl$_3$ | MeOH | MilliQ | CHCl$_3$ | MeOH | MilliQ | PCI | CHCl$_3$ | MeOH | MilliQ | PCI |
| 1 | 0 | 500 | 0 | 500 | 0 | 200 | 0 | 500 | 500 | 200 | 0 |
| 2 | 0 | 250 | 250 | 625 | 375 | 0 | 0 | 625 | 625 | 250 | 0 |
| 3 | 0 | 250 | 250 | 0 | 0 | 0 | 500 | 0 | 250 | 250 | 500 |
| 4 | 156.25 | 312.5 | 31.25 | 343.75 | 187.5 | 168.75 | 0 | 500 | 500 | 200 | 0 |
| C | 0 | 0 | 0 | 500 | 500 | 200 | 0 | 500 | 500 | 200 | 0 |

* "MilliQ" in the table represents Milli-Q water.

5-2 Results

The preservation of a fecal sample in the absence of the organic solvent (i.e., no preservation solvent) ("Method C" of Table 9) at 4° C. or room temperature or the preservation in a 50% methanol solution ("Method 2" and "Method 3" of Table 9) at 4° C. or room temperature was confirmed to have a higher rate of increase or decrease in metabolite concentrations as compared with the preservation at −80° C. (FIG. 11). On the other hand, the preservation of a fecal sample in a 100% methanol solution ("Method 1" of Table 9) at 4° C. or room temperature or the preservation in a methanol-chloroform solution ("Method 4" of Table 9) at 4° C. or room temperature exhibited metabolite profiles similar to those of preservation at −80° C. and suppressed increase or decrease in metabolite concentrations caused by preservation (FIGS. 11 and 12).

These results indicate that: when a fecal sample is preserved under refrigeration or at ordinary temperature, metabolite profiles vary; and by contrast, the preservation of a fecal sample in an organic solvent such as a 100% methanol solution or a methanol-chloroform solution can suppress the degree of these variations in metabolite profiles and favorably maintain metabolite profiles in the fecal sample immediately after harvesting.

INDUSTRIAL APPLICABILITY

According to the present invention, one or more substances (preferably, intestinal metabolites) can be efficiently extracted from a fecal sample. According to the present invention, more types of substances can be extracted from a fecal sample. Accordingly, the present invention can provide a method for extracting substances from a fecal sample, the method being suitable for conducting analyses such as metabolomic analysis using mass spectrometry or nuclear magnetic resonance spectrometry, and metagenomic analysis using a next-generation sequencer.

The invention claimed is:

1. A method for extracting one or more substances from a fecal sample derived from a human, comprising:
   step A-1 of subjecting the fecal sample to disruption and suspending treatment with beads having a diameter in a range of 0.02 to 0.5 mm, in any one of the following solvents (a) to (g) to obtain a suspension:
   (a) a solvent comprising an aqueous solvent and a hydrophilic organic solvent, and not comprising a hydrophobic organic solvent, wherein a content of the aqueous solvent is in the range of 10 to 50% by weight, and a content of the hydrophilic organic solvent is in the range of 90 to 50% by weight;
   (b) a solvent comprising an aqueous solvent and a hydrophobic organic solvent and not comprising a hydrophilic organic solvent, wherein a content of the aqueous solvent is in the range of 10 to 50% by weight, and a content of the hydrophobic organic solvent is in the range of 90 to 50% by weight;
   (c) a solvent comprising an aqueous solvent, a hydrophilic organic solvent and a hydrophobic organic solvent, wherein a content of the aqueous solvent is in the range of 5 to 60% by weight, a content of the hydrophilic organic solvent is in the range of 10 to 70% by weight, and a content of the hydrophobic organic solvent is in the range of 10 to 70% by weight;
   (d) a solvent comprising a hydrophilic organic solvent, and not comprising an aqueous solvent or a hydrophobic organic solvent;
   (e) a solvent comprising a hydrophobic organic solvent, and not comprising an aqueous solvent or a hydrophilic organic solvent;
   (f) a solvent comprising a hydrophilic organic solvent and a hydrophobic organic solvent, and not comprising an aqueous solvent; and
   (g) water;
   step B of separating a liquid layer comprising the solvent from the suspension; and
   step C of removing proteins from the liquid layer and then obtaining the one or more substances,
   the method further comprising, before the step A-1, step X of drying the fecal sample derived from a human, and subjecting the dried fecal sample to disruption treatment with beads having a diameter in a range of 0.6 to 15 mm to obtain dried fecal small pieces, wherein the dried fecal small pieces are used as the fecal sample of the step A-1.

2. The method for extracting one or more substances according to claim 1, wherein the solvent used in the step A-1 is the solvent (a), wherein the solvent (a) comprises water and methanol, and wherein a content of water in the solvent is in a range of 10 to 50% by weight, and a content of methanol is in a range of 90 to 50% by weight.

3. The method for extracting one or more substances according to claim 1, wherein the solvent used in the step A-1 is the solvent (c), and wherein the solvent (c) comprises water, methanol, and chloroform, and a content of water in the solvent is in a range of 10 to 50% by weight.

4. The method for extracting one or more substances according to claim 1, further comprising, before the step A-1, step Y of preserving a fecal sample harvested from a human in the following solvent (h) or (i), wherein the fecal sample thus preserved in the step Y is used as the fecal sample of the step A-1:
   (h) a solvent comprising an aqueous solvent and 75% by weight or more of a hydrophilic organic solvent, and not comprising a hydrophobic organic solvent; and
   (i) a solvent comprising an aqueous solvent, a hydrophilic organic solvent and a hydrophobic organic solvent.

5. The method for extracting one or more substances according to claim 1, wherein the aqueous solvent is selected from the group consisting of water, an aqueous solution of salt, and an aqueous buffer solution.

6. The method for extracting one or more substances according to claim 1, wherein the hydrophilic organic solvent is one or more solvents selected from the group consisting of methanol, ethanol, propanol, isopropanol, butanol, isobutanol, acetonitrile, dimethyl sulfoxide, dimethylformamide, dimethylacetamide, acetone, tetrahydrofuran and diethylene glycol.

7. The method for extracting one or more substances according to claim 1, wherein the hydrophobic organic solvent is one or more solvents selected from the group consisting of chloroform, hexane, ether, diethyl ether, benzene, phenol, and isoamyl alcohol.

8. A method for identifying one or more substances in a fecal sample, and measuring a concentration, composition or proportion of the one or more substances, comprising:
   step P of separating the one or more substances extracted by the method according to claim 1 by chromatography or capillary electrophoresis, and conducting mass spectrometry and/or nuclear magnetic resonance spectrometry to identify the one or more substances, and to measure the concentration, composition or proportion of the one or more substances.

9. A method for classifying a plurality of subjects into two or more clusters, comprising:

step Q of conducting the method according to claim 8 on each of fecal samples obtained from the plurality of subjects to identify two or more substances and to measure a concentration, composition or proportion of the two or more substances; and step S of conducting cluster analysis on data of the concentration, composition or proportion of the two or more substances obtained in the step Q, and classifying the plurality of subjects into two or more clusters according to similarity of substance profiles.

10. The method according to claim 9, further comprising, between the step Q and the step S, step R of standardizing the data of the concentration, composition or proportion of the two or more substances obtained in the step Q, wherein the data standardized in the step R is used in the cluster analysis in the step S.

11. The method for extracting one or more substances according to claim 1, wherein the solvent used in the step A-1 is the solvent (a), and wherein the solvent (a) comprises water and methanol, a content of water in the solvent is in a range of 10 to 50% by weight, and a content of methanol is in a range of 90 to 50% by weight.

\* \* \* \* \*